(12) United States Patent
Pak et al.

(10) Patent No.: US 11,896,267 B2
(45) Date of Patent: Feb. 13, 2024

(54) CONTROLLER MODULE FOR STRUT ADJUSTMENT

(71) Applicant: Stryker European Operations Limited, Carrigtwohill (IE)

(72) Inventors: Chulho Pak, Mahwah, NJ (US); Subash K. Mannanal, Mahwah, NJ (US); Peter Sterrantino, Jacksonville, FL (US); Noah Roberson, Mahwah, NJ (US); Anup Kumar, Gurgaon (IN); Andrew J. Nelson, New City, NY (US)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 18/160,780

(22) Filed: Jan. 27, 2023

(65) Prior Publication Data

US 2023/0255665 A1 Aug. 17, 2023

Related U.S. Application Data

(60) Provisional application No. 63/310,174, filed on Feb. 15, 2022.

(51) Int. Cl.
*A61B 17/62* (2006.01)
*A61B 17/66* (2006.01)
*A61B 17/64* (2006.01)

(52) U.S. Cl.
CPC .............. *A61B 17/62* (2013.01); *A61B 17/66* (2013.01); *A61B 17/645* (2013.01)

(58) Field of Classification Search
CPC ........ A61B 17/62; A61B 17/66; A61B 17/645
USPC .................................................... 606/56–58
See application file for complete search history.

(56) References Cited

U.S. PATENT DOCUMENTS

| 8,834,467 | B2 | 9/2014 | Singh | |
|---|---|---|---|---|
| 9,101,398 | B2 | 8/2015 | Singh | |
| 10,010,350 | B2 | 7/2018 | Mannanal | |
| 10,082,384 | B1* | 9/2018 | Singh | A61B 34/10 |
| 2007/0225704 | A1* | 9/2007 | Ziran | A61B 17/66 |
| | | | | 606/57 |

(Continued)

FOREIGN PATENT DOCUMENTS

| EP | 2919683 A1 | 9/2015 |
|---|---|---|
| KR | 102090906 B1 | 3/2020 |
| WO | 2022024133 A1 | 2/2022 |

*Primary Examiner* — Eduardo C Robert
*Assistant Examiner* — David C Comstock
(74) *Attorney, Agent, or Firm* — SLEMAN & LUND LLP

(57) ABSTRACT

An external fixation system may include first and second fixation rings and a plurality of adjustable length struts. Each adjustable length strut may have two joints, a rod, a tube, and an actuator configured to drive the rod axially relative to the tube to change an effective length of the strut. The system may include a plurality of controller modules each configured to couple to a corresponding strut. The external fixation system may have a manual mode of operation in which the controller modules are not coupled to the struts, and manual actuation of the actuators changes the effective lengths of the struts in discrete length increments. The external fixation system may have an automated mode of operation in which the controller modules are coupled to the struts, and automated actuation of the actuators changes the effective lengths of the struts in infinitesimally small length increments.

17 Claims, 31 Drawing Sheets

(56) References Cited

U.S. PATENT DOCUMENTS

| | | | | |
|---|---|---|---|---|
| 2012/0330312 A1* | 12/2012 | Burgherr | ................ | A61B 90/98 |
| | | | | 606/54 |
| 2015/0080892 A1* | 3/2015 | Lehmann | ............... | A61B 17/66 |
| | | | | 606/57 |
| 2017/0071632 A1* | 3/2017 | Vikinsky | ................ | A61B 17/62 |
| 2018/0228515 A1* | 8/2018 | Ross | .................. | A61B 17/6491 |
| 2022/0354539 A1* | 11/2022 | Ferrante | ................. | A61B 17/62 |

* cited by examiner

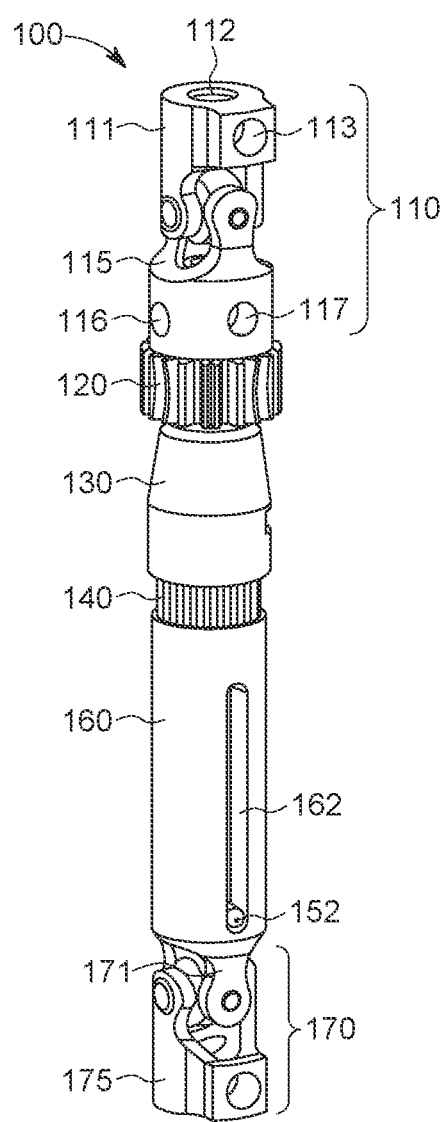
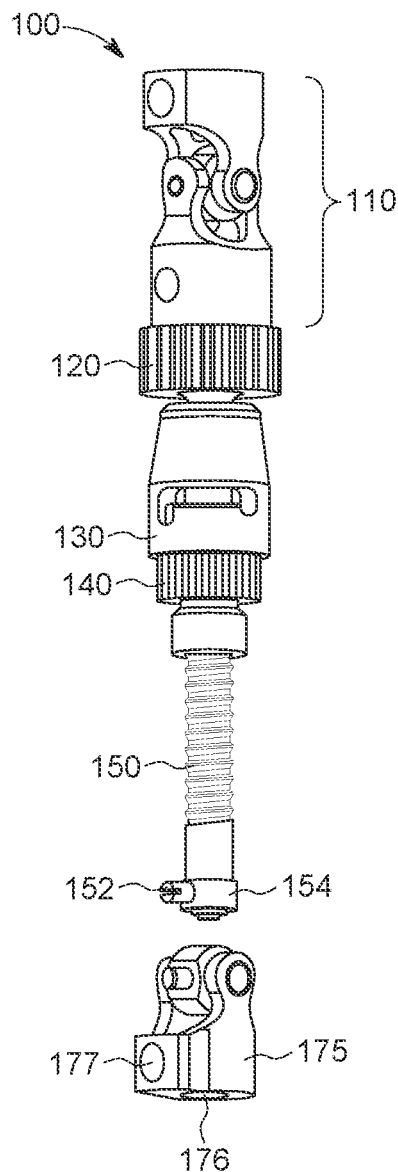
FIG. 2A
FIG. 2B

CONTROLLER MODULE FOR STRUT ADJUSTMENT

CROSS-REFERENCE TO RELATED APPLICATIONS

This application claims priority to the filing date of U.S. Provisional Patent Application No. 63/310,174, filed Feb. 15, 2022, the disclosure of which is hereby incorporated by reference herein.

BACKGROUND OF THE DISCLOSURE

The present disclosure relates to systems and components of external fixation frames. More particularly, the present disclosure relates to struts and strut components using gear mechanisms and/or controller modules for manipulation of an external fixation frame.

Many different types of bone deformities can be corrected using external fixation systems to perform the distraction osteogenesis process. For example, an Ilizarov device or similar external fixation system may be used. Such systems generally use rings also designated as fixation plates connected by threaded rods or struts for manipulation, lengthening, angulation, rotation, and/or translation of deformities of bones.

As the struts are manipulated, the rings or fixation plates change positions relative to one another, causing the bones or bone segments attached to the fixation plates to change positions relative to one another, until the bone segments are in a desired position relative to one another. Fixation systems have many areas which may be improved including, for example, the ease and precision with which the fixation system may be adjusted by a user, whether a clinician or a patient.

BRIEF SUMMARY

An external fixation system may include a first fixation ring configured to couple to a first bone portion of a patient, and a second fixation ring configured to couple to a second bone portion of the patient. The system may include a plurality of adjustable length struts, each adjustable length strut having a first joint proximate a first end of the strut, a second joint proximate a second end of the strut opposite the first end, a rod, a tube that receives the rod, and an actuator configured to drive the rod axially relative to the tube to change an effective length of the strut. The system may also include a plurality of controller modules, each controller module configured to couple to a corresponding strut. In an assembled condition of the external fixation system, the plurality of struts couple the first fixation ring to the second fixation ring. The external fixation system has a manual mode of operation in which there is no coupling between any of the plurality of controller modules and any of the plurality of struts, and manual actuation of one of the actuators is configured to change the effective length of the corresponding strut in discrete length increments. The external fixation system has an automated mode of operation in which each of the controller modules is coupled to the corresponding strut, and automated actuation of one of the actuators is configured to change the effective length of the corresponding strut in infinitesimally small length increments. It should be understood that the same plurality of adjustable length struts may be capable of either manual or automated operation, so the inclusion of two different types of struts in inventory (e.g. one type for manual operation, another type for automated operation) is not necessary.

The actuator of each strut may include a strut knob and a strut gear, the strut knob being translatable relative to the strut gear between a first axial position relative to the strut gear and a second axial position relative to the strut gear. When the strut knob is in the first axial position relative to the strut gear, the strut knob may be constrained from rotation relative to the strut, and when the strut knob is in the second axial position relative to the strut gear, the strut knob may be rotatable relative to the strut. In the manual mode of operation, a biasing member may bias the strut knob to the first axial position. In the manual mode of operation, each discrete length increment may correspond to a discrete increment of rotation of the strut knob relative to the strut. In the manual mode of operation, when the strut knob is in the second axial position relative to the strut gear, the biasing member may be prevented from transitioning the strut knob to the first axial position between each discrete increment of rotation. In the automated mode of operation, the controller module may maintain the strut knob in the second axial position relative to the strut gear. In the automated mode of operation, a controller gear of the controller module may interface with the strut gear. Each controller module may include a motor configured to rotate the controller gear. Each controller module may include a collar with at least one prong, and when the controller modules is coupled to the corresponding strut, the at least one prong is positioned between the strut gear and the strut knob. The at least one prong may include a tip portion with a ramped surface, the ramped surface configured to drive the strut knob to the second axial position as the controller module is coupled to the corresponding strut. The collar may include a first extension and a second extension defining a distance therebetween, the distance being about equal to a width of a securement area of the strut, the first and second extensions configured to abut the securement area of the strut when the controller module is coupled to the strut to secure the controller module to the strut. The first extension may be flexible and may include a transverse projection extending toward the second extension, a reduced distance between the transverse projection and the second extension being smaller than the width of the securement area of the strut. As the controller module is coupled to the strut, contact between the transverse projection and the securement area of the strut may cause the first extension to flex away from the strut until the transverse projection clears an end of the securement area and the first extension snaps back toward the securement area so that the transverse projection impedes the controller module from uncoupling from the strut. When the external fixation system is in the automated mode of operation, each controller module may have a dynamization mode configured to cycle between increasing and decreasing the effective length of the strut to axially dynamize the strut with effective length adjustments that are smaller than the discrete length increments in the manual mode of operation. In the assembled condition of the external fixation system, the external fixation system may have a stable construction, and while each controller module is operating in the dynamization mode cycling between increasing and decreasing the effective length of the corresponding strut, the external fixation system may remain in the stable construction.

According to another aspect of the disclosure, a method of implementing a correction plan to correct a deformity in a bone of a patient includes various steps. The method may include coupling a first fixation ring to a first portion of the bone of the patient, and coupling a second fixation ring to a second bone portion of the bone of the patient. The method may also include coupling the first fixation ring to the second fixation ring with a plurality of adjustable length struts, each strut having a first joint proximate a first end of the strut, a second joint proximate a second end of the strut opposite the first end, a rod, a tube that receives the rod, and an actuator configured to drive the rod axially relative to the tube to change an effective length of the strut. The method may further include providing a plurality of controller modules, each controller module configured to couple to a corresponding strut. The correction plan may be implemented using either (i) a manual mode of operation or (ii) an automated mode of operation. In the manual mode of operation, there is no coupling between any of the plurality of controller modules and any of the plurality of struts, and manual actuation of one of the actuators changes the effective length of the corresponding strut in discrete length increments. In the automated mode of operation, each of the controller modules is coupled to the corresponding strut, and automated actuation of one of the actuators is capable of changing the effective length of the corresponding strut in infinitesimally small length increments. The method may also include coupling the plurality of controller modules to the corresponding struts, and implementing the correction plan using the automated mode of operation. The method may also include operating one of the controller modules in a dynamization mode to cycle between increasing and decreasing the effective length of the corresponding strut to axially dynamize the strut with effective length adjustments that are smaller than the discrete length increments available in the manual mode of operation. The method may further include operating one of the controller modules in the dynamization mode is performed during a correction phase in which all of the plurality of struts have not yet reached a corresponding final effective length. The method may also include operating one of the controller modules in the dynamization mode is also performed in a consolidation phase in which all of the plurality of struts have reached the corresponding final effective length.

BRIEF DESCRIPTION OF THE DRAWINGS

FIG. 2A is a perspective view of a strut of the external fixation system of FIG. 1.

FIGS. 2B-C are a perspective views of the strut of FIG. 2A with certain components omitted.

FIG. 2D is a perspective view of an actuation mechanism of the strut of FIG. 2A.

DETAILED DESCRIPTION

Figure 1:
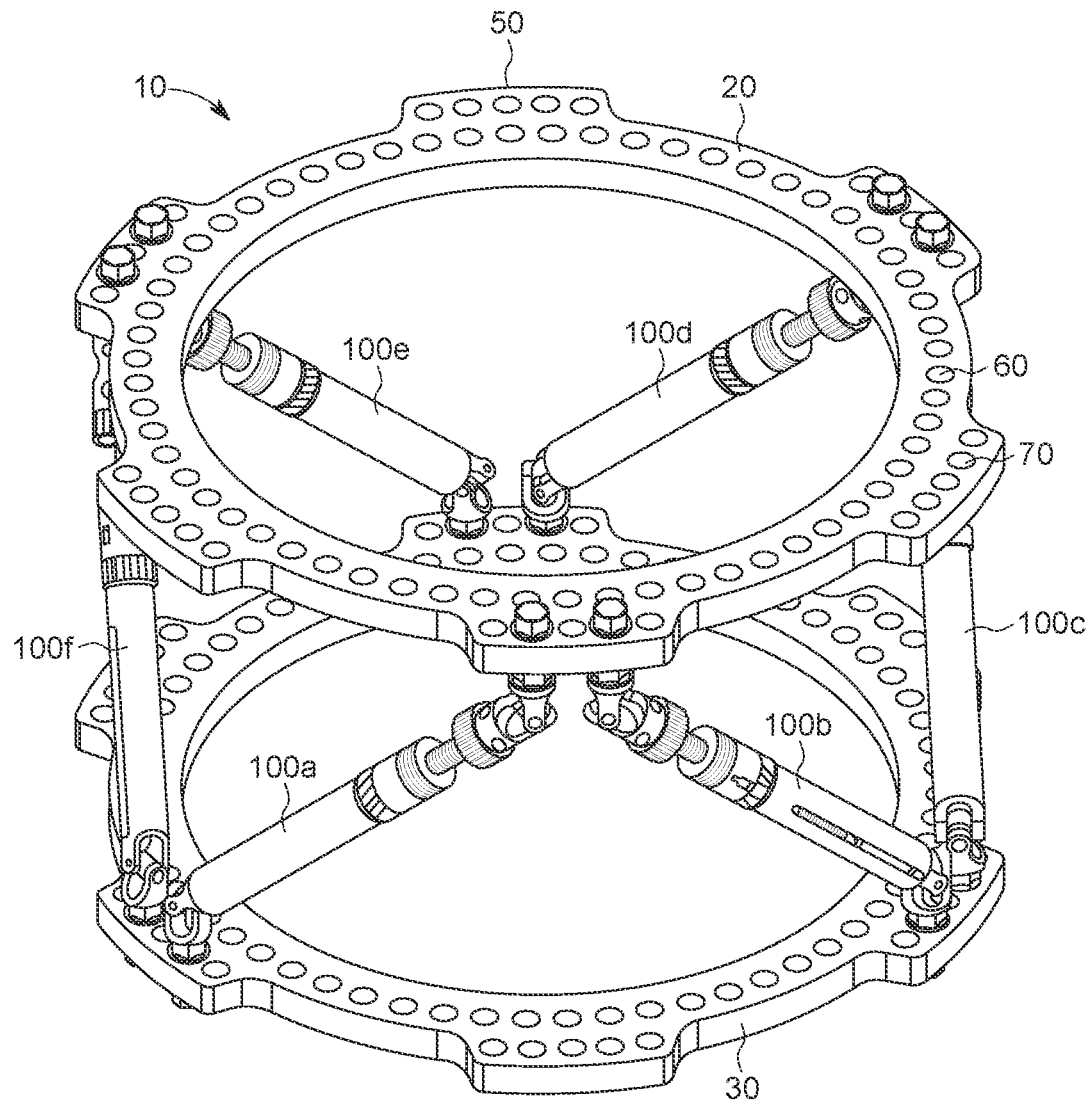
FIG. 1 is a perspective view of an external fixation system according to an embodiment of the disclosure.

FIG. 1 shows an external fixation frame 10 in an assembled condition according to one aspect of the disclosure. Generally, fixation frame 10 includes a first ring 20 and a second ring 30, with six adjustable length telescopic struts 100a-f coupling the first ring 20 to the second ring 30. The first ring 20 may also be referred to as a proximal ring or a reference ring, while the second ring 30 may also be referred to as a distal ring or a moving ring. In the illustrated embodiment, each strut 100a-f includes a threaded portion that may thread into or out of a tube portion, for example by interaction with quick release mechanism 130, to decrease or increase the length, respectively, of the telescopic strut. Each end of each strut 100a-f may be coupled to the first ring 20 and second ring 30 via a joint mechanism, such as a ball joint, a constrained hinge joint, or a universal joint as illustrated. The use of universal joints on each end of the strut provides for six degrees of freedom of motion of the external fixation system 10. It should be understood that although the disclosure is generally described in the context of closed circular rings, the concepts described herein may apply with equal force to other types of rings, such as open rings and/or U-shaped rings.

In external fixation system 10, telescopic struts 100a-f are used to reduce fractures and correct deformities over time. Patients correct the deformities by prescribed adjustments of the struts 100a-f. The lengths of the struts 100a-f are adjusted over time to change the position and orientation of the two rings 20, 30 with respect to one another, which in turn repositions and reorients the bone fragments, with a goal of correcting the bone deformity. The adjustment of the external fixator 10 should strictly comply with the predetermined correction plan.

Rings 20 and 30 of external fixation system 10 may include a plurality of extension tabs 50. In the illustrated example, each ring 20 and 30 includes six extension tabs 50 spaced circumferentially around the perimeter of the respective rings, although more or fewer may be suitable depending on the particular components of the fixation system. In addition to what is described directly below, extension tabs 50 may help increase the cross-sectional area of rings 20, 30 and thus provide for increased stiffness of the rings.

With this configuration, each ring 20, 30 includes a first inner circumferential row of holes 60 and a second outer circumferential row of holes 70. As illustrated, the second outer circumferential row of holes 70 may be only positioned on the plurality of extension tabs 50 on the rings 20 and 30. It should be understood that although the second outer circumferential row of holes 70 is shown in FIG. 1 as being positioned solely on extension tabs 50, top ring 20 and/or bottom ring 30 may contain two complete rows of holes, for example with a completely circular (or nearly completely circular) geometry. The use of extension tabs 50, compared to two full circumferential rows of holes, may help reduce overall bulk of rings 20, 30 and also provide for intuitive strut placement for surgical personnel. The completely circular version of rings 20, 30 with two full (or nearly full) rows of circumferential holes may be particularly suited for relatively small diameter rings, although indentations or other features may be introduced to provide an intuitive interface for strut placement by surgical personnel. Further, in the illustrated embodiment, the first and second circumferential rows of holes 60 and 70 are positioned so that the first row of holes 60 does not align radially with the second row of holes 70. In other words, the first row of holes 60 has a staggered configuration with respect to the second row of holes 70. The additional hole options may also be utilized for connecting other components, such as fixation pins to couple the rings 20, 30 to the respective bone fragments. Still further, the staggered configuration of holes between the first and second rows 60, 70 may also help prevent interference between components attached to nearby holes, for example such as a strut 100a-f positioned in a first hole and a fixation pin or other fixation member attached to an adjacent or nearby second hole. For example, a relatively thin wire extending radially from one of the holes in the first circumferential row 60 may not radially interfere with a hole positioned in the second circumferential row 70 because of the radial staggering. It should be understood that the size of the tabs 50 may increase or decrease depending on the diameter of the rings 20 and 30, with greater diameter rings 20 and 30 having larger tabs 50 with more holes 70 compared to smaller diameter rings. For example, the illustrated tabs 50 include six holes 70, and a smaller ring may include smaller tabs with four holes each, for example.

FIG. 2A illustrates a perspective view of one telescopic strut 100 from the external fixation system 10 of FIG. 1. It should be understood that the components of struts 100a-f may be identical to one another, although some struts 100a-f may have different sizes than other struts 100a-f and may include different indicia, such as colors or markings for identification purposes, as described in greater detail below. For purposes of this disclosure, the term proximal refers to the top of the strut 100 in the orientation of FIG. 2A, and the term distal refers to the bottom of the strut 100 in the orientation of FIG. 2A. The proximal end portion of strut 100 may include a first joint 110, which is shown in this example as a universal joint. Joint 110 may include a proximal portion 111, which may include a first aperture 112 aligned substantially parallel with the longitudinal axis of strut 100 and a second aperture 113 aligned substantially transverse or orthogonal to the first aperture 112. The first aperture 112 may be configured to receive a fastener that passes through a hole in proximal ring 20 to secure the proximal portion 111 of joint 110 to proximal ring 20. The fastener may be connected so that the proximal portion 111 does not rotate relative to proximal ring 20. The second aperture 113 may be configured to receive a portion of a tool to prevent proximal portion 111 from rotating, for example while a fastener is being screwed into or otherwise inserted into first aperture 112. Joint 110 may also include a distal portion 115 with a first aperture 116 and a second aperture 117, the first and second apertures 116, 117 being aligned substantially transverse and/or orthogonal to one another and to the longitudinal axis of strut 100. First and second apertures 116, 117 may be used as attachment points for attaching additional components to strut 100.

Still referring to FIG. 2A, strut 100 may include additional components including an actuation mechanism 120, a quick-release mechanism 130, a strut identifier 140, a threaded rod 150 (not visible in FIG. 2A), a tube 160, and a second joint 170. As noted above, the effective length of strut 100, which may be thought of as the distance between the proximal end and distal end of strut 100, may be adjusted by threading the threaded rod 150 of strut 100 into or out of tube 160 through interaction with quick-release mechanism 130.

Figures 2C, 2D:
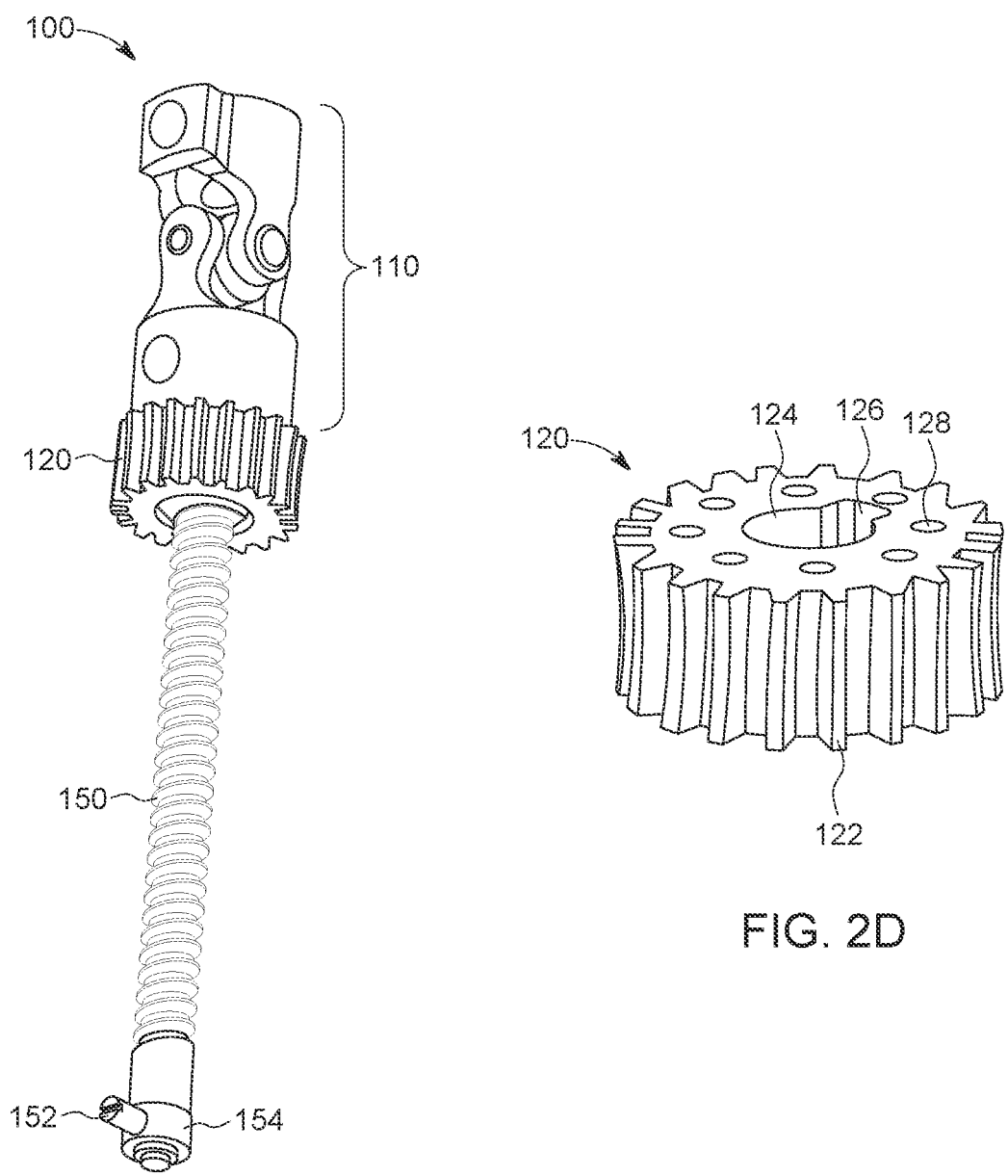

FIG. 2B illustrates strut 100 with tube 160 omitted for clarify of illustration. FIG. 2C illustrates strut 100 with tube 160, as well as quick-release mechanism 130, strut identified 140, and second joint 170 omitted for clarity of illustration.

Actuation mechanism 120 is shown isolated in FIG. 2D. Actuation mechanism 120 may be generally a short, cylindrical component with a plurality of ridges or gear teeth 122 extending around the circumference of actuation mechanism 120. The actuation mechanism 120 may be rotatably coupled to threaded rod 150 so that rotation of actuation mechanism 120 causes a corresponding rotation of threaded rod 150. For example, actuation mechanism 120 may have a channel 124 extending therethrough, with an extension 126 in channel 124 that mates with a corresponding extension in threaded rod 150, so that rotation of actuation mechanism 120 causes rotation of threaded rod 150. It should be understood that the threaded rod 150 may rotate with respect to the first joint 110, with portions of the first joint 110 and second joint 170 being rotatably fixed to rings 20 and 30, respectively. The proximal surface of actuation mechanism may include a plurality of divots or grooves 128 sized to accept a ball which is biased into the groove via a spring. The spring may have a first end in contact with a distal surface of first joint 110, with a distal end pressing a ball into the proximal surface of actuation mechanism 120. With this configuration, an amount of force is required to rotate actuation mechanism 120 to overcome the force of the spring pushing the ball into the divot 128. As rotation of actuation mechanism 120 continues, the ball will eventually be positioned adjacent to an adjacent groove 128. As rotation continues further, the spring will force the ball into the next groove 128 when the ball is aligned with the groove 128, causing a tactile and/or audible click. Each "click" may correspond to a particular axial change in length so that a user knows, for example, that four "clicks" correspond to 1 mm of length adjustment. Similar "clicking mechanisms" are described in greater detail in U.S. Pat. No. 8,834,467, the contents of which are hereby incorporated by reference herein.

Referring now to FIGS. 2A-B, quick-release mechanism 130 may generally take the form of an outer housing that surrounds a portion of threaded rod 150. Quick-release mechanism 130 may have a disengaged state and an engaged state. In the disengaged state, threaded rod 150 may be capable of moving into or out of tube 160 without rotation of the threaded rod 150, for quick adjustments of the length of strut 100, which may be useful for example while initially assembling the fixation frame 10. Rotating the quick-release mechanism 130 may transition the quick-release mechanism 130 into the engaged state, in which threaded rod 150 may only move axially into or out of tube 160 via rotation of the threaded rod 150. The mechanism for keeping the quick-release mechanism 130 in the engaged state may include a ball or other feature that is forced between adjacent threads of threaded rod 150 so that axial translation of the threaded rod 150 is only possible via rotation, so that rotation of threaded rod 150 axially moves the threaded rod 150 into the tube 160, without requiring the tube 160 to have internal threading. It should be understood that the quick-release mechanism 130 is not a necessary component of strut 100, and may be omitted from strut 100 if desired. If quick-release mechanism 130 is omitted, it may be preferably to include internal threads on tube 160 to correspond to external threads on threaded rod 150. Further details of quick-release mechanisms have been described elsewhere, including, for example, in U.S. Pat. No. 9,101,398, the contents of which are hereby incorporated by reference herein.

A strut identifier 140 may be coupled to strut 100 at any desired location, for example between the quick-release mechanism 130 and the tube 160. Strut identifier 140 may take the form of a clip or any other suitable shape that can be quickly and securely clipped onto the strut 100 and removed from strut 100. For example, in the illustrated embodiment, strut identifier 140 is a "C"-shaped clip that is flexible enough to open for easy connection to strut 100, but rigid enough that the strut identifier 140 is not easily removed from strut 100 without intentional application of force. Strut identifier 140 may have a color or other identifier such as a number, letter, or shape pattern. Each strut 100a-f may have a strut identifier 140 that is structurally similar or identical, but that each has easily distinguishable indicia, such as different colors, different numbers, etc. Strut identifiers 140 may be used so that each strut 100a-f is easily distinguished from one another, and so that other matching indicia may be provided on other components, described in greater detail below, that may be added onto struts 100a-f so that each additional component may be easily matched with the correct corresponding strut 100a-f. Strut identifier 140 may also function to prevent unintentional disengagement of the quick release mechanism 130.

Referring again to FIG. 2A, tube 160 may be a generally hollow cylindrical tube configured to allow threaded rod 150 to move axially into or out of tube 160 to decrease or increase the effective length of strut 100, respectively. As noted above, such axial movement may be produced by rotation of threaded rod 150 when the quick release mechanism 130 is in the engaged position, so that the threads of the threaded rod 150 engage the ball or other mechanism within the quick release mechanism 130. If omitting the quick release mechanism 130, the tube 160 may include internal threads that mate directly with the external threads of the threaded rod 150. A slot 162 may extend along part of the length of the tube 160, the slot 162 opening the hollow inside of the tube 160 to the exterior of the tube. The slot 162 may have a width slightly larger than the width of button 152. Referring now to FIGS. 2B-C, the distal end of threaded rod 150 may include a button 152 coupled to a collar 154, the collar 154 surrounding the distal end of threaded rod 150. Collar 154 may be positioned with a groove at the distal end of threaded rod 150 so that collar 154 may rotate freely around the axis of the strut 100 while being axially fixed with respect to the threaded of 150. Referring again to FIG. 2A, as threaded rod 150 is threaded into or out of tube 160, button 152 travels up or down the slot 162 of the tube 160, which is possible because button 152 and collar 154 are free to rotate with respect to threaded rod 150. Tube 160 may include indicia, such as hash marks and/or measurements, on or adjacent to slot 162. The position of button 152 along slot 162 may correspond to the effective length of the strut 100, so that a user can easily determine the effective length of the strut based on the indicia adjacent to the position of button 152 at any particular time.

Referring still to FIG. 2A, the distal end of tube 160 may include two extensions that form a proximal portion 171 of second joint 170. Second joint 170 may include a distal portion 175 that, together with proximal portion 171 and an internal mechanism form a universal joint similar to first joint 110. Distal portion 175 may include a first aperture 176 that is aligned substantially parallel with strut 100. Aperture 176 may be adapted to receive a fastener therein to couple second joint 170 to distal ring 30. The fastener may be a screw or other type of fastener, and may be adapted to tightly couple the second joint 170 to the distal ring 30 so that the second joint 170 does not rotate with respect to distal ring 30. With this configuration, the slot 162 of tube 160 may be positioned outward (away from the center of proximal and distal rings 20, 30) so that the position of button 152 with respect to indicia on tube 160 may be easily read at all times. The distal portion 175 of second joint 170 may include a second aperture 177 aligned substantially orthogonal to first aperture 176 and adapted to receive a tool to keep second joint 170 from rotating, for example while a fastener is screwed into first aperture 176. This may help ensure, for example, the slot 162 of tube 160 is facing away from the center of the rings 20, 30 as the strut 100 is tightened to the rings 20, 30. It should also be understood that in some prior art devices, rotational freedom of the strut was provided by loosely coupling the joint(s) to the ring(s) so that the joints themselves could swivel. In the present disclosure, the rotational degree of freedom is provided by the ability of threaded rod 150 to rotate, while the tight attachment of the first joint 110 and second joint 170 to the first ring 20 and second ring 30 provides for a more stable connection.

It should be understood that strut 100 as described above may be designed for manual actuation, for example by a user gripping the actuation mechanism 120 with his hand and manually rotating the actuation mechanism 120. However, it should be understood that a tool may be used, either directly on actuation mechanism 120 or with intervening components, to adjust the length of strut 100. Such a tool is described in greater detail below.

Although one exemplary strut 100 is shown and described in connection with FIGS. 2A-D, it should be understood that other struts may be used instead of struts 100 in an external fixation system such as that shown in FIG. 1. For example, FIGS. 3A-F illustrate various views of a strut 200 (or portions thereof) that may be used instead of strut 100. It should be understood that many components of strut 200 are similar or identical to corresponding components of strut 100, and parts that are similar or identical are provided with a part number increased by 100. For example, first joint 110 of strut 100 may be similar to first joint 210 of strut 200. These corresponding components, unless noted otherwise, are identical between strut 100 and strut 200. Thus, for purposes of brevity, each component of strut 200 is not described in detail, particularly when the component is identical to a component of strut 100 that has already been described above.

Figure 3A:
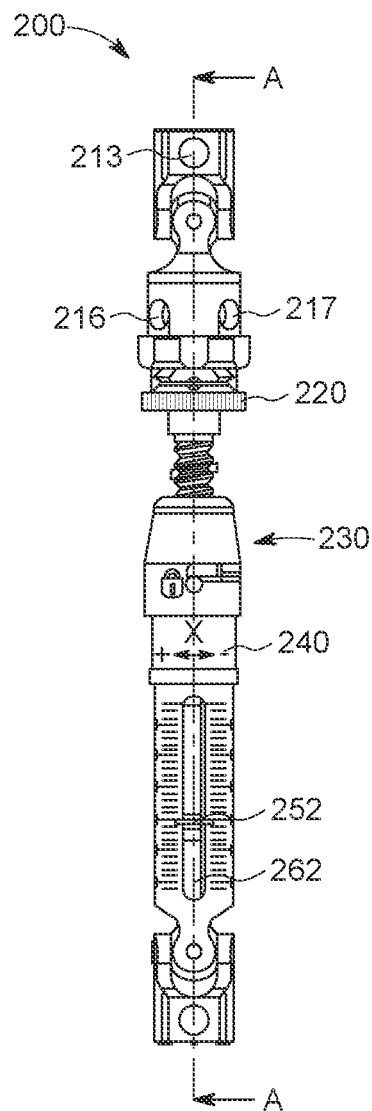
FIG. 3A is a front view of another embodiment of a strut for use with an external fixation system similar to that shown in FIG. 1.
Figure 3B:
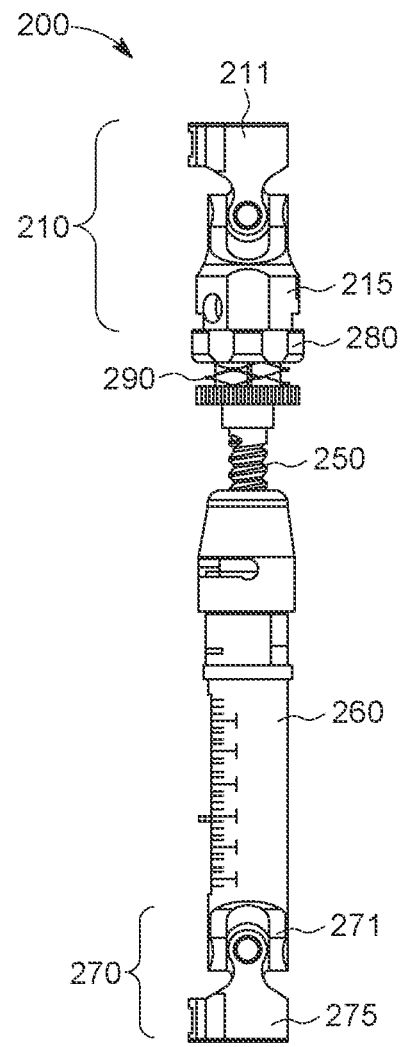
FIG. 3B is a side view of the strut of FIG. 3A.
Figures 3C, 3D:
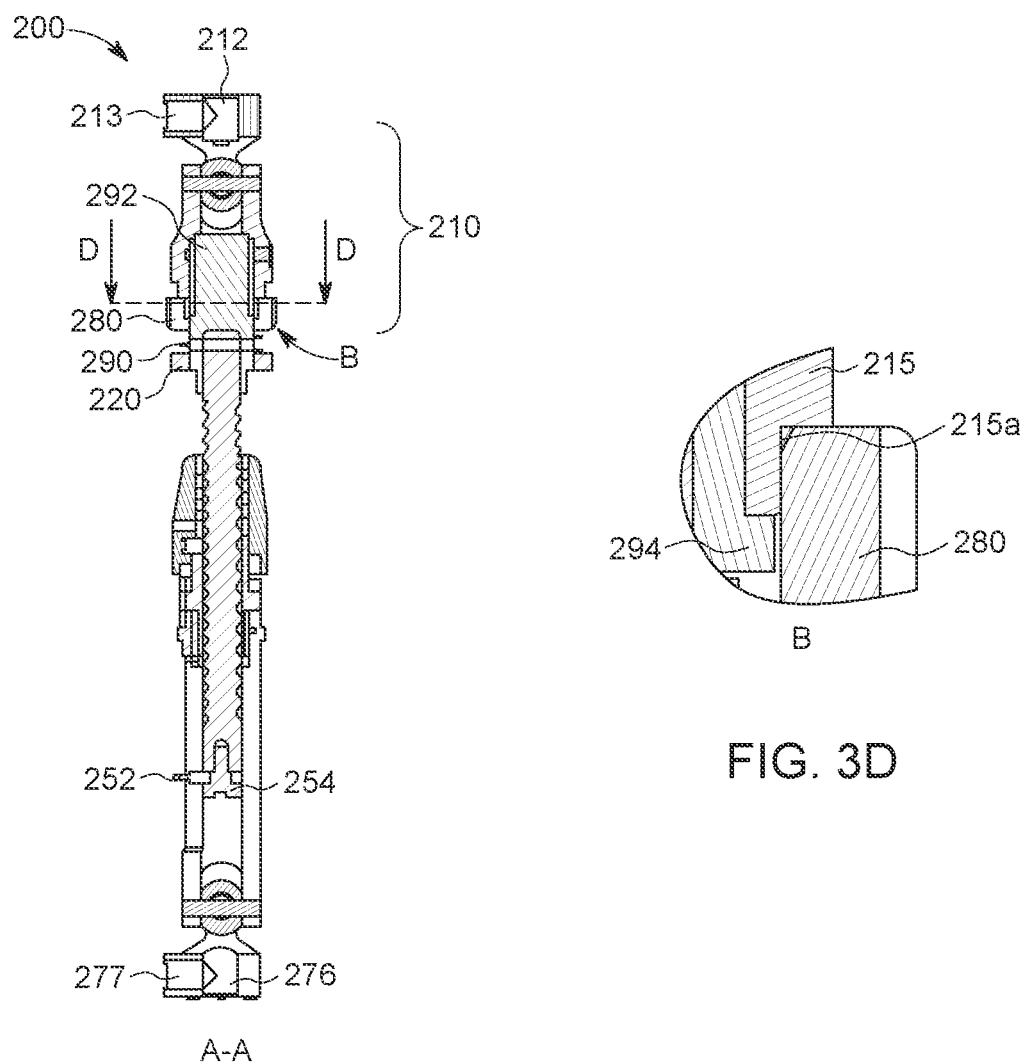
FIG. 3C is a cross-section of the strut of FIG. 3A taken along section A-A of FIG. 3A.
FIG. 3D is an enlarged view of Section B of the strut of FIG. 3C.
Figure 3E:
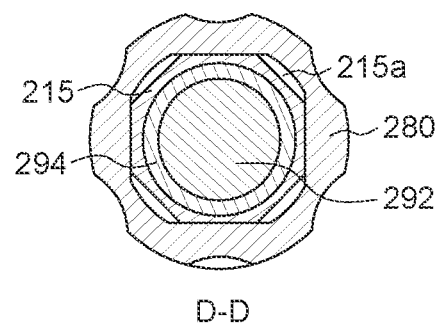
FIG. 3E is a cross-section of the strut of FIG. 3C taken along section D-D of FIG. 3C.
Figure 3F:
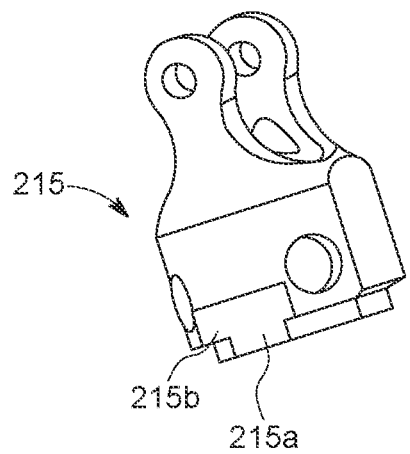
FIG. 3F is a perspective view of a distal portion of a first joint of the strut of FIG. 3A.

Referring generally to FIGS. 3A-C, first joint 210 may be substantially identical to first joint 110, except that the distal portion 215 of first joint 210 may include a plurality of flats. In the illustrated embodiment, the distal portion 215 of first joint 210 includes two opposing flats 215b (e.g. spaced 180 degrees apart) to mate with, or otherwise contact, corresponding flats on another device. However, it should be understood that more than two flats, or fewer than two flats (including zero flats) may be provided depending on the structure of the corresponding device that may couple to the distal portion 215 of first joint 210. Although not separately illustrated, one or both of apertures 216 and 217 may include threading, such as internal threading, to threadedly mate with external threads of a component of another device. Referring briefly to FIGS. 3D-F, the distal portion 215 of first joint 210 may include a terminal end with a plurality of flats 215a. In the illustrated embodiment, the terminal end includes eight flats 215a in an octagonal configuration, although in other embodiments more or fewer flats 215a may be provided, with the number of flats corresponding (although not necessarily on a 1-1 basis) to the number of flats on thumbwheel 280, described in greater detail below.

Referring to FIGS. 3A-E, thumbwheel 280 may be positioned fully or partially surrounding the terminal end of the distal portion 215 of first joint 210. Thumbwheel 280 may include grooves and recesses, or other textures to help provide an easier user grip. It should be understood that, although the term thumbwheel is used, thumbwheel 280 may be considered a knob, actuator, or other rotatable member. As shown in FIG. 3E, the interior surface of thumbwheel 280 may have a general square (with or without rounded interior edges) shape, the inner diameter of thumbwheel 280 being similar to the outer diameter of the terminal end of the distal portion 215 of first joint 210. As is described in greater detail below, the inclusion of eight flats 215a with four interior flats of the thumbwheel 280 allows for the distal portion 215 of the first join 210 to have eight rotational positions relative to the thumbwheel 280 in 45 degree rotational increments.

Strut 200 may include an actuation mechanism 220, which may be in the form of a gear with gear teeth. Gear 220 need not include the dimples described in connection with gear 120. A biasing mechanism, such as wave spring 290, may be positioned between gear 220 and thumbwheel 280 so that the ends of the wave spring 290 press against the gear 220 and thumbwheel 280. Referring to FIG. 3C, the thumbwheel 280, wave spring 290, and gear 220 may all be positioned over a shaft 292 which is positioned within the distal portion 215 of first joint 210. The gear 220 may be both axially and rotationally fixed to shaft 292. A sleeve 294, shown in more detail in FIGS. 3D and 3G, may be positioned between the exterior of shaft 292 and the interior of the distal portion 215 of first joint 210, with bearings 296 allowing for rotation of the shaft 292 relative to the distal portion 215 of first joint 210, while maintaining the relative axial positions between the shaft 292 and the distal portion 215 of first joint 210. The process for manual use of the thumbwheel 280 to increase or decrease the effective length of strut 200 is described below following the description of the remaining components of strut 200.

Strut 200 may include a quick-release mechanism 230 that is substantially similar or identical to quick-release mechanism 130, and is thus not described in further detail here. Strut 200 may also include a strut identifier 240 substantially similar to strut identifier 140. Strut identified 240 may include other information, including indicia, such as a "plus" and "minus" sign, to help indicate to a user which direction of rotation, for example of thumbwheel 280, will increase or decrease the strut length upon manual actuation. However, this type of information may be provided elsewhere in addition to, or instead of, strut identifier 240. As with strut 200, the quick release mechanism 230 may be omitted, in which case the rod 250 may instead be directly threaded into tube 260. In the illustrated embodiment, the threaded rod 250 of strut 200 extends into tube 260, which forms part of second joint 270. As shown in FIG. 3C, a button 252 may be coupled to a fastener 254 that is couple to a bottom of the threaded rod 250. The button may extend through the slot 262 and have a flat end that protrude through the slot 262 and which may be wider than the slot 262. The tube 260 may include hash marks or other indicia which indicate a length of the strut depending on the relative position between the button 252 and the indicia. The fastener 254 may be capable of substantially free rotation about its longitudinal axis relative to the threaded rod 250 so that, as the threaded rod 250 rotates and drives into or out of tube 260, the button 252 is capable of riding up or down within slot 262. It should be understood that the button 152 and collar 154 of strut 100 may instead be used with strut 200, and similarly the button 152 and collar 154 of strut 100 may be replaced with the button 252 and fastener 254 of strut 200.

Figure 3G:
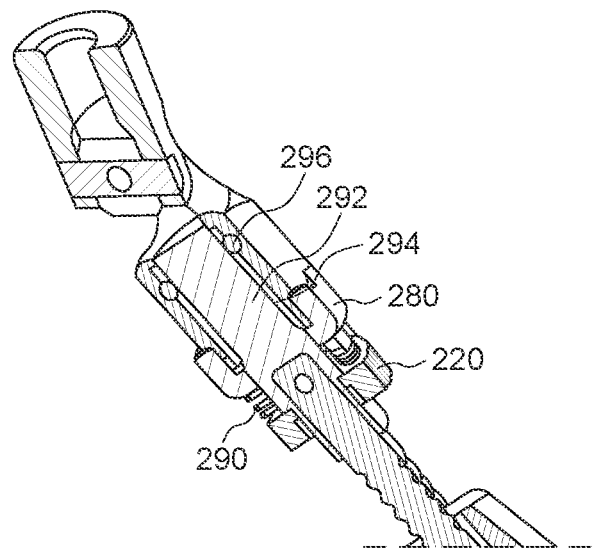
FIGS. 3G-H are sectional views of a portion of the strut of FIG. 3A undergoing actuation.
Figure 3H:
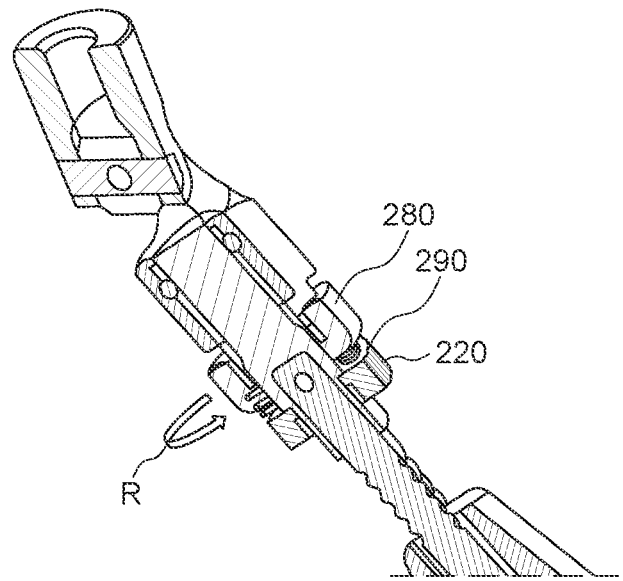

An exemplary manual actuation of strut 200 to increase or decrease its effective length is illustrated in FIGS. 3G-H. Although not shown in FIGS. 3G-H, it should be understood that strut 200 may be coupled to rings 20, 30 as described above in connection with strut 100, and the strut 200 may first (prior to or after attachment to the rings 20, 30) have its length rapidly adjusted by unlocking the quick release mechanism 230, and axially translating the threaded rod 250 relative to the tube 260 until the desired length is reached, as described in context with strut 100. In order to perform fine manual adjustment of the length of strut 200, the thumbwheel 280 is gripped by the user, whether the user is a physician, patient, or other personnel. In the absence of applied force, the wave spring 290 forces the inner flats of thumbwheel 280 into contact with the flats 215a of the distal portion 215 of first joint 210, as shown in FIG. 3G. Because the first joint 210 does not rotated about its longitudinal axis, the thumbwheel 280 cannot be rotated when in this unbiased condition. The user must compress wave spring 290 by pulling or pushing the thumbwheel 280 distally, as shown in FIG. 3H. With enough compression of the wave spring 290, the interior flats of the thumbwheel 280 clear the flats 215a of the distal portion 215 of first joint 210, allowing for rotation of the thumbwheel 280 in a rotational direction R. The thumbwheel 280 may be rotationally fixed to the shaft 292, for example via corresponding flats. Thus, as the thumbwheel 280 is rotated while the wave spring 290 is compressed, the shaft 292 also rotates, causing the threaded rod 250, which is rotationally fixed to the shaft 292, to telescope into or out of the tube 260, depending on the direction of rotation. As the thumbwheel 280 rotates, the wave spring 290 tends to press the thumbwheel 280 proximally. However, when the interior flats of the thumbwheel 280 are out of alignment with corresponding pairs of flats 215a, the thumbwheel 280 is restricted from any proximal movement. However, upon reaching alignment of the flats via enough rotation, the wave spring 290 tends to press the thumbwheel 280 back into a locked position preventing further rotation. With this particular embodiment of eight flats 215a and a substantially square interior of the thumbwheel 280, there is alignment between the flats after each 45 degrees of rotation. However, it should be understood that other numbers and geometries of corresponding flats may be used to provide rotational increments of more or less than 45 degrees.

With the manual actuation described above, each discrete rotational increment (which is 45 degrees in the illustrated embodiment) may correspond to a particular adjustment of the effective length of the strut 200. The spring action of the wave spring 290 interacting with the thumbwheel 280 may provide for clear tactile, audible (e.g. clicking) and/or visual feedback of each discrete rotational increment of the thumbwheel 280. Thus, the user may be instructed to perform a given number of rotations of the thumbwheel 280 at particular times on particular days for each strut 200 to provide the desired incremental change of the struts 200 and rings 20, 30. The discrete rotational increments may provide particular ease of use for the patient if the patient is in charge of manually adjusting the lengths of struts 200 according to a particular correction plan. It should also be understood that the interaction between the thumbwheel 280, the wave spring 290, and the flats 215a may provide for a locking mechanism in which the length of the strut 200 is unlikely to be unintentionally adjusted, for example by accidental contact with the thumbwheel 280.

It should be understood that, although struts 100 and 200 are illustrated and described as separate embodiments, components described in connection with strut 100 may be used, where appropriate, in addition to or instead of components described in connection with strut 200, and vice versa. Further, strut 100 may be configured for use with a modular attachment member, such as that described in U.S. Pat. No. 10,010,350, the disclosure of which is hereby incorporated by reference herein. Strut 200, on the other hand, may be configured for use with controller modules described below. However, it should be understood that either strut (with any required modifications) may be used with either modular attachment to switch between manual and automated (or semi-automated) adjustment.

While struts 200 provide for user-friendly manual adjustments of the effective length of struts 200, in some circumstances it may be preferable to provide for automated adjustment of the struts 200 that involves little or no user input, for example to minimize the likelihood of user error. Despite the ease of use of manual adjustment of struts 200, patients (as opposed to physicians or other professionals) may be particularly prone to missing prescribed manual length adjustments, or incorrectly adjusting the length of struts 200 manually. However, it may be inconvenient to have one type of strut 200 that can only be manually adjusted, with another different type of strut that may be automatically adjusted. Thus, strut 200 is designed for use with a controller module 300 that may be coupled to strut 200 so that strut 200 can be automatically adjusted. This configuration may provide other benefits, including the ability to attach controller modules 300 outside the operating theater, meaning that the controller modules 300 do not need to be sterilized for use.

Figure 4A:
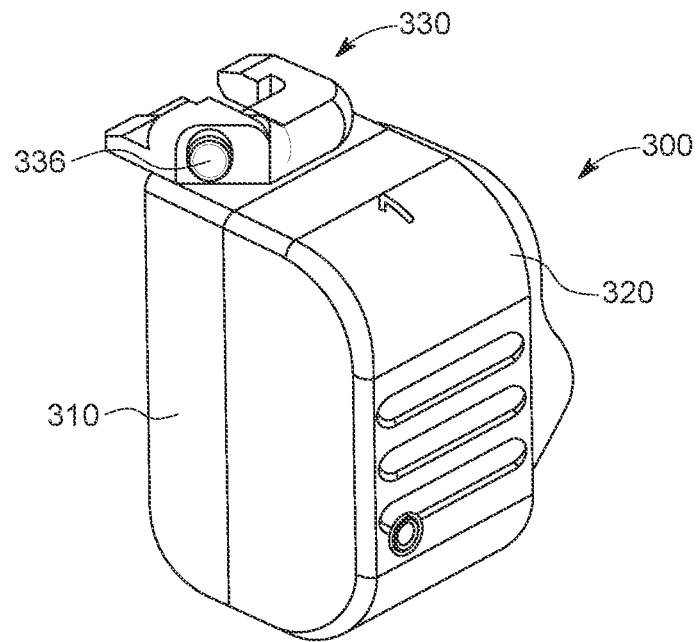
FIGS. 4A-B are front and rear perspective views, respectively, of a controller module for use with the strut of FIG. 3A.
Figure 4B:
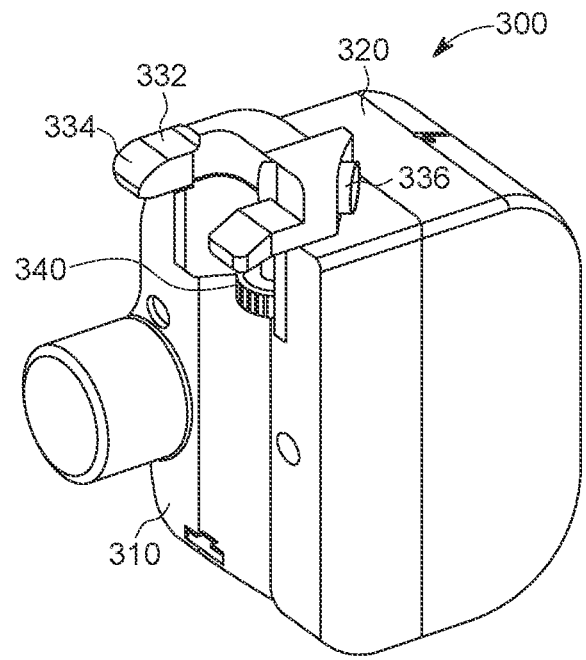

FIGS. 4A-B show front and rear perspective views of one embodiment of controller module 300. Generally, controller module 300 may include a rear housing 310 and a front cover 320. A plurality of controller modules 300 may be provided to a user in a kit, for example six controller modules 300 if six struts 200 are provided. Each controller module 300 may be identical, and the kit may come with stickers or other identifiers that may be applied to the controller modules 300, and those stickers or other identifiers may correspond to identifiers (such as strut identifiers 240 or other identifiers) that may be applied to struts 200. With this configuration, each strut 200 may have an identifier that corresponds to an identifier on a corresponding controller module 300 that will be used with that particular strut. In other embodiments, each cover 320 may be provided with a pre-printed or pre-applied identifier.

Controller module 300 may include a collar 330, for example coupled to the rear housing 310 and extending rearward, which may interface with strut 200. In the illustrated embodiment, collar 330 is generally "U"-shaped and includes two prongs 332 that define an open space therebetween. Each prong 332 may terminate in portion with a ramped surface 334. The inner side surfaces of the prongs 332 that confront one another may be substantially flat, and have a spacing and geometry that generally corresponds to the two opposing flat surfaces 215b of the distal portion 215 of first joint 210. The collar 330 may also include an extension portion that receives a fastener 336 therein. The fastener 336 may be captured within the collar 330 so that it cannot unintentionally disconnect from the system. The fastener 336 may take the form of a screw with external threading that may be configured to be screwed into one of the apertures 216, 217 of the first joint 210 of strut 200 to secure the controller module 300 to the strut 200. In some embodiments, two fasteners 336 may be provided with collar 330. However, it may be preferable to include only a single fastener 336 to allow for different orientations of the controller module 300 relative to the strut 200, for example because the strut 200 may include more apertures than the controller module includes fasteners. A gear system 340 may extend through an opening in rear housing 310, with the gear system 340 (or a portion thereof) configured to mesh with gear 220 of strut 200. Various internal components of controller module 300 are described in further detail prior to describing the interaction between the controller module 300 and the strut 200.

Figure 4C:
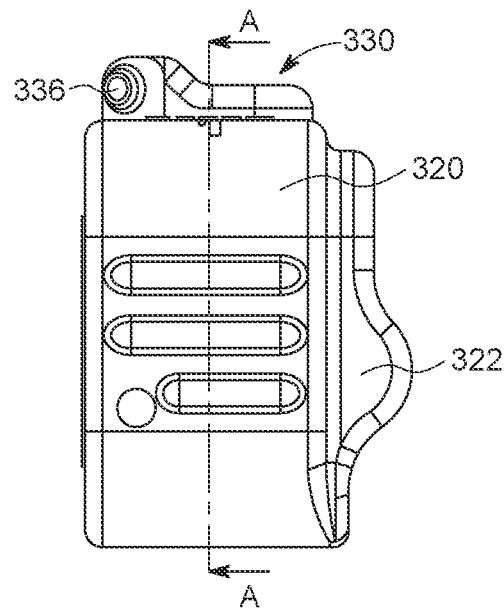
FIGS. 4C-E are front, rear, and bottom views, respectively, of the controller modules of FIGS. 4A-B.
Figure 4D:
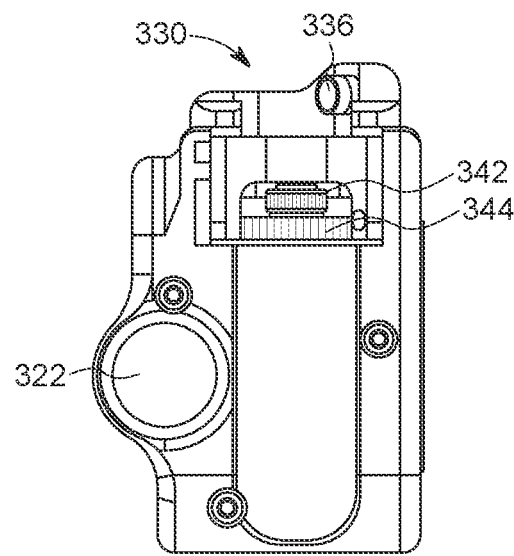
Figure 4E:
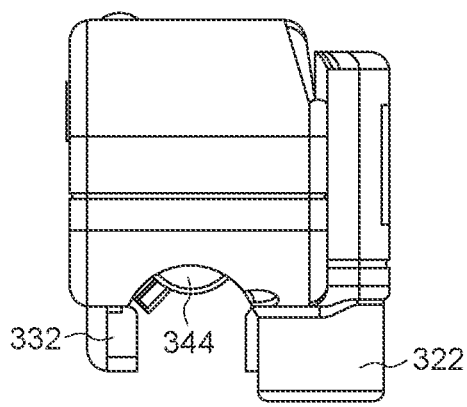
Figure 4F:
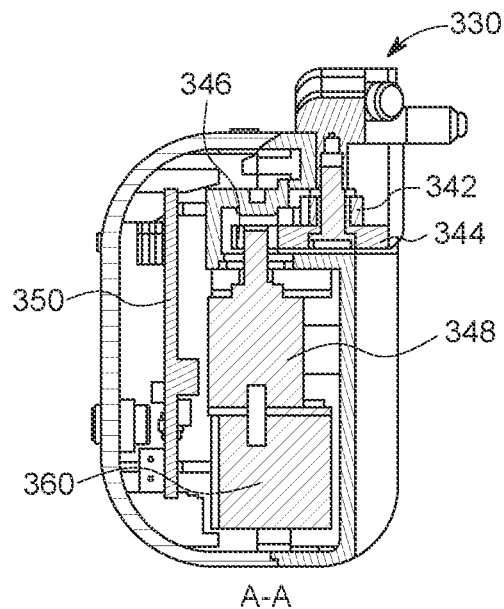
FIG. 4F is a cross-section of the controller module of FIG. 4C taken along section line A-A of FIG. 4C.
Figure 4G:
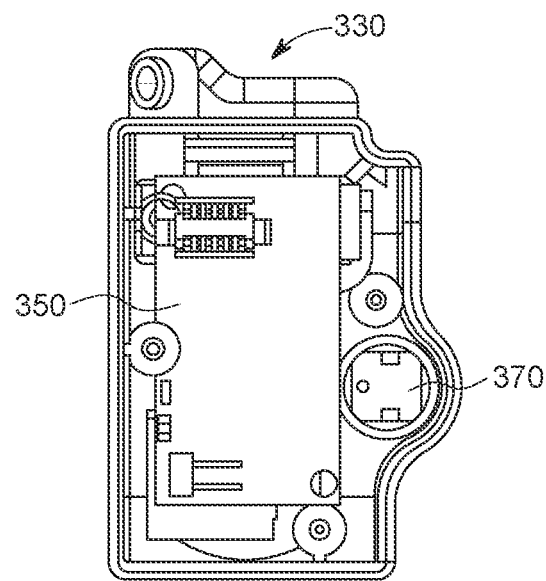
FIGS. 4G-I are front, bottom, and side views, respectively, of the controller module of FIG. 4A with a cover removed from a rear housing.
Figure 4H:
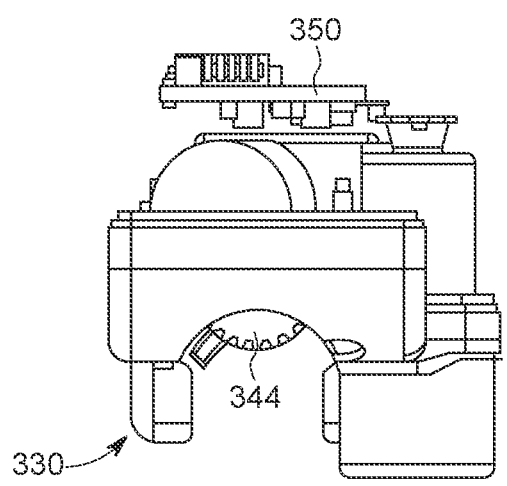
Figure 4I:
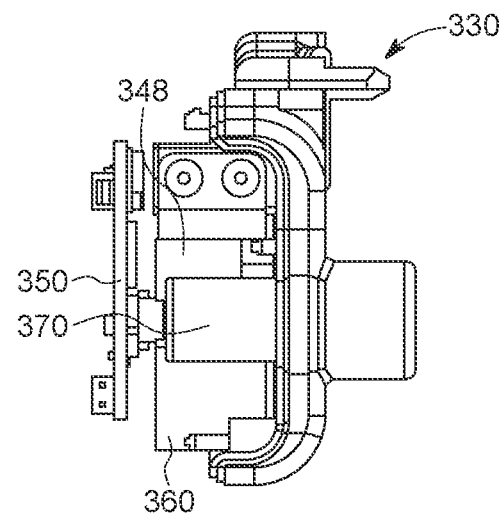

FIGS. 4C-E are front, rear, and bottom views, respectively, of the controller module 300, and FIG. 4F is cross-section of the controller module. To help better illustrate internal components, FIGS. 4G-I are front, bottom, and side views, respectively, of the controller module 300 with front cover 320 removed. Referring generally to FIGS. 4A-I, the controller module 300 may include one or more batteries 370, one or more controllers 350 (e.g. a PCB), and a motor 360. The controller 350 may be operatively coupled to memory storage, which may for example include instructions (e.g. a correction schedule) for adjusting the lengths of struts 200 (or one particular strut 200 that the controller module 300 will be attached to). The controller 350 may be capable of one or both of wired or wireless communication with another device, for example a mobile phone or computer, to allow for instructions and/or data to be uploaded or downloaded, as well as for actuation to be initiated. The battery 370 may provide power to allow for operation of the controller 350 and/or the motor 360. In the illustrated embodiment, the rear housing 310 and cover 320 collectively form a battery compartment 322 to house the battery 370 therein. However, it should be understood that if the battery 370 has a different size or shape, the battery compartment 322 may correspondingly have a different size or shape. In some embodiments, the batteries 370 may be off-the-shelf batteries. The battery compartment 322 may include a feature, like a slot, so that the battery compartment 322 may be easily opened with a screwdriver, a coin, or a similar device.

The motor 360 may be an electric motor adapted to drive gear system 340. The gear system 340 may include a first gear 348, such as a planetary gear, directly actuated or rotated by the motor 360. The first gear 348 may be coupled to a motor gear 346 which may mesh with a relatively large gear 344, which is in turn coaxially connected to a relatively small gear 342. With this configuration, activation of motor 360 results in rotation of gear 342, which may mesh with gear 220 of strut 200, described in greater detail below. It should be understood that any suitable gear system may be utilized in order to cause rotation of a gear meant to mesh with gear 220 of strut 200 upon activation of motor 360, and thus other gear systems than that illustrated may be suitable for use.

Figure 5A:
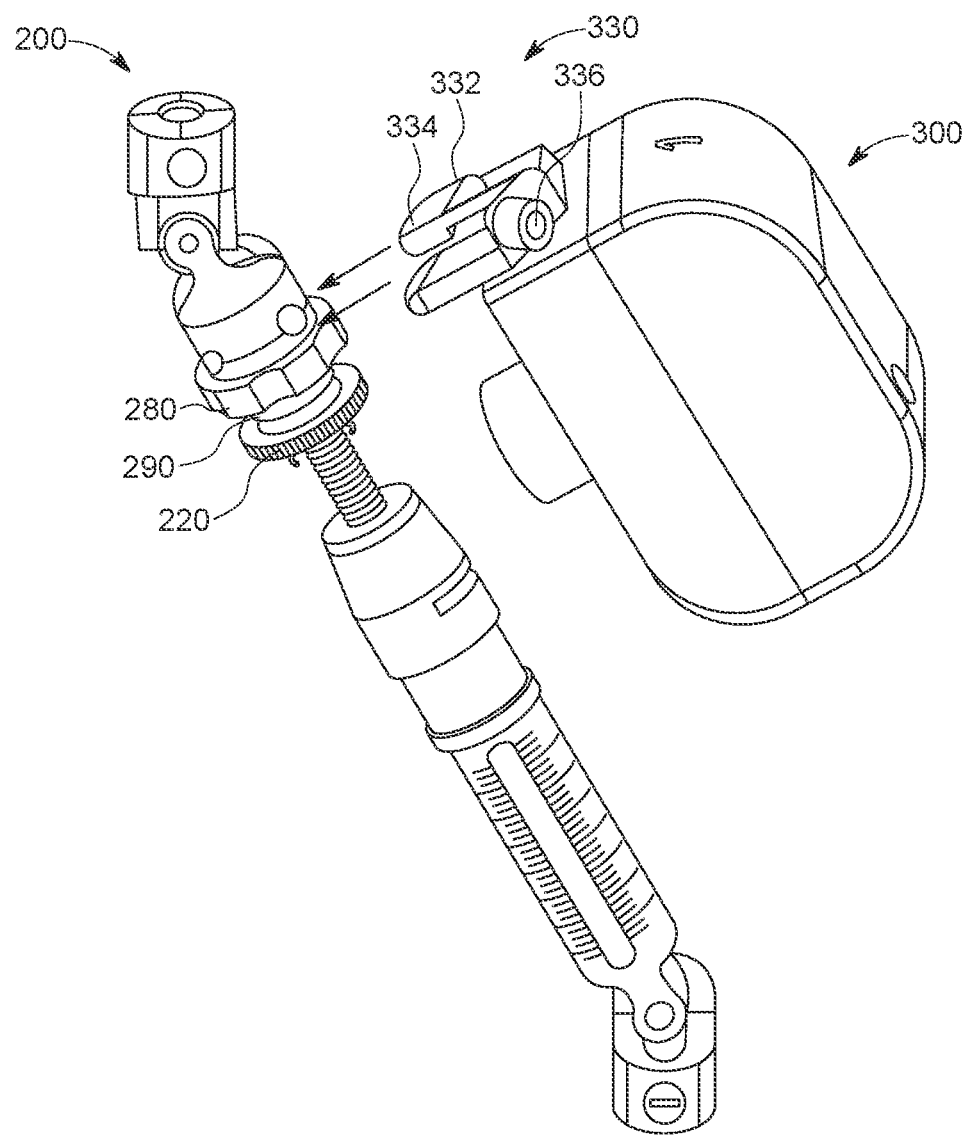
FIG. 5A is a perspective view of the controller module of FIG. 4A being coupled to the strut of FIG. 3A.
Figure 5B:
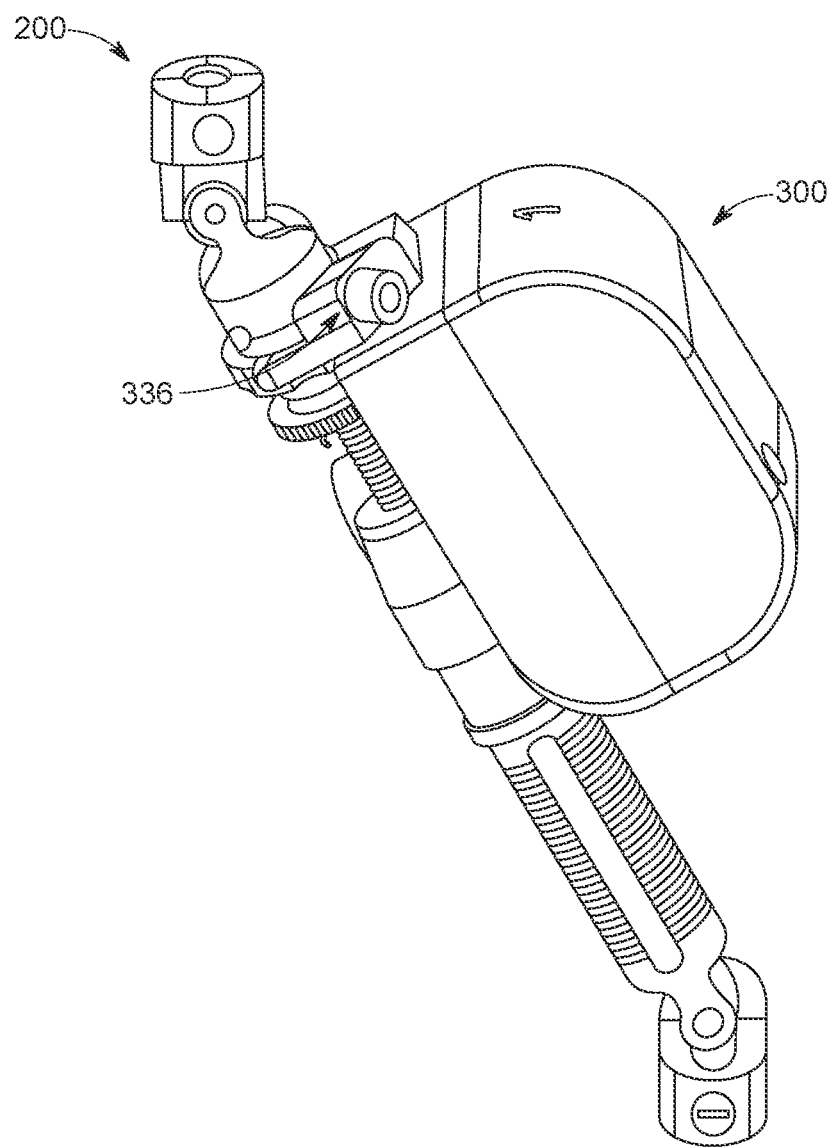
FIG. 5B is a perspective view of the controller module of FIG. 4A coupled to the strut of FIG. 3A.
Figure 5C:
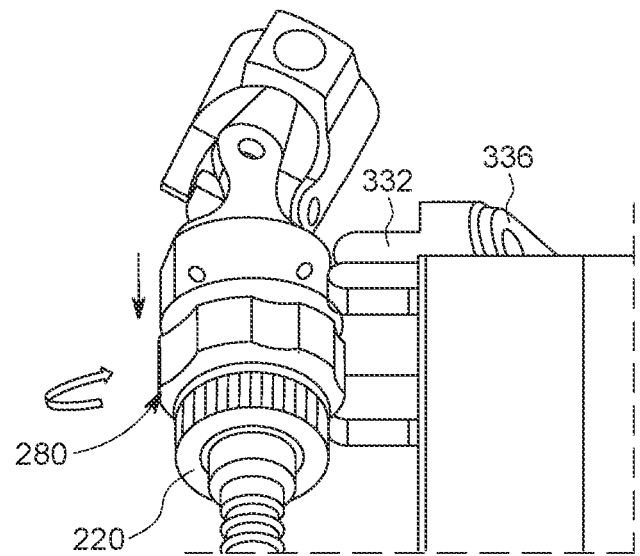
FIGS. 5C-D are enlarged views of the coupling process shown in FIGS. 5A-B, respectively.
Figure 5D:
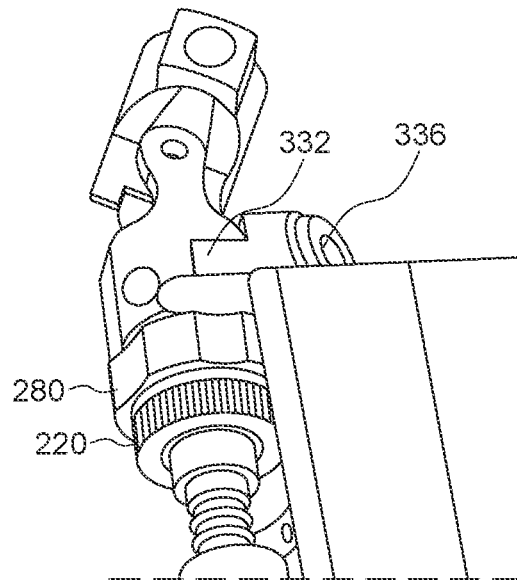

FIGS. 5A-D show the controller module 300 being coupled to strut 200. FIGS. 5A and 5C illustrate the controller module 300 just before coupling to the strut 200, and FIGS. 5B and 5D illustrate the controller module 300 just after coupling to the strut 200. Preferably, if the controller modules 300 are to be coupled to the struts 200, the coupling is not performed until after the external fixation system 10 is assembled and coupled to the patient. In this manner, the controller modules 300 do not need to be sterilized, as they never need to enter a sterile operating field. However, it should be understood that this order of operations is not a requirement, and the controller modules 300, if they are to be coupled to the struts 200, may be coupled prior to or during assembly of the external fixation system 10 to the patient.

Prior attaching controller module 300 to strut 200, the quick-release mechanism 230 (if such a quick release mechanism is included) is preferably in a locked condition. In addition, prior to coupling controller module 300 to strut 200, the wave spring 290 is in a relatively uncompressed condition (e.g. as shown in FIG. 3G) such that the wave spring 290 forces the inner flats of thumbwheel 280 into contact with the flats 215a of the distal portion 215 of first joint 210, as shown in FIG. 3G. The prongs 332 of the collar 330 are advanced along the distal portion 215 of first joint 210, so that the ramped surfaces 334 wedge between the top of thumbwheel 280 and the bottom of the surface of the first joint adjacent flats 215b. As the prongs 332 advance, the ramped surfaces 334 help force the thumbwheel 2880 downward toward gear 220, compressing wave spring 290 in the process. In order to further secure the controller module 300 to the strut 200, fastener 336 may be rotated to thread into corresponding threads of one of apertures 216 or 217. When controller module 300 is coupled to the strut 200, the gear 342 of the controller module 300 meshes with gear 220 of strut 200, such that rotation of gear 342 causes a corresponding rotation of gear 220 (and thus a corresponding change in length of strut 200).

It should be understood that, when the controller module 300 is coupled to strut 200, the wave spring 290 remains compressed and the thumbwheel 280 remains clear of the flats 215a of the distal portion 215 of first joint 210. In other words, when controller module 300 is not coupled to the strut 200, the length strut 200 can be manually adjusted by manually pushing and rotating the thumbwheel 280, with the wave spring 290 "snapping" the thumbwheel 280 upward into a locked position at the end of each rotational increment. As described above, this manual operating modality allows a user to manually adjust the length of the strut by rotating the thumbwheel 280 a pre-determined number of "clicks," with the discrete rotational increments helping ensure the user is able to easily follow the strut length adjustment prescription. However, when the controller module 300 is coupled to the strut 200, the permanent compression of wave spring 290 fully disengages the discrete rotational feature of the thumbwheel 290 because the thumbwheel 290 is permanently clear of the flats 215a while the wave spring 290 is compressed. Thus, the controller module 300 is able to adjust the length of strut 200 in infinitesimally small increments by rotating the gear 342, and thus gear 220, in increments that are as small or as large as desired to achieve the desired strut length adjustment. It should be understood that, when the term "infinitesimally small" is used herein, it is generally meant that the increments of strut length adjustment are only limited by the ability of the motor of the strut controller to drive the relevant gears in very small increments. There may effectively be some lower limit to the length increment that the motor of the controller module can adjust the strut, but in practice that limit, if it exists, would be extremely small compared to typical minimum incremental length adjustments available in manually adjustable struts. Further, although the controller module 300 may be able to adjust the length of strut 200 in infinitesimally small increments, in practice the controller module may be programmed to adjust the length of strut 200 in discrete amounts at discrete times (e.g., by a quarter turn every 6 hours, a half turn twice a day, etc.)

In one exemplary method, a patient undergoing an external fixation procedure may have fixation rings 20, 30 fixed to the patient's bone, for example on opposite sides of a bone deformity, and the struts 200 (e.g. six struts) may be used to attach the two rings 20, 30 to one another. This may be performed while the quick release mechanisms 230 of the struts 200 are in an unlocked condition so that rapid or coarse adjustment of the struts 200 is possible. With the struts 200 in the desired positions and orientations, the quick release mechanisms 230 (if included) may be transitioned to the locked condition to allow for gradual length adjustment going forward. The surgery may then be completed.

Following completion of surgery (or prior to surgery), a correction schedule may be created to indicate how the length of each strut 200 should be adjusted over time to achieve the desired correction of the bone deformity. In one example, the deformity correction schedule may indicate how many "clicks" each strut 200 should be adjusted each time period (e.g. every 6 hours, every 12 hours, etc.). As should be understood, the "clicks" may correspond to rotational increments of the thumbwheel 280 relative to flats 215a, and may be intended for use during manual operation only. As noted above, when the controller module 300 is coupled to the strut 200, the "clicking" mechanism is disengaged. Alternately, or in addition, the correction schedule may be created to indicate the length that each strut 200 needs to be adjusted over time, without reference to "clicks."

If it is desired to have automated strut length adjustments, following the surgery (or during the surgery), a controller module 300 may be coupled to each strut 200. For example, a strut 200 labeled "strut 1" or with some other indicium (e.g. a red color) may be coupled to a corresponding controller module 300 labeled "module 1" or with some other corresponding indicium (e.g. a red color). Each controller module 300 may be uploaded with the corresponding adjustment length schedule for that corresponding strut 200. This may be performed via wired or wireless connection between a computer (or similar device) and the controller module 300. The battery 370 in each controller module 300 may provide the power to operate the motor 360 to, in turn, operate gear system 340 to adjust the length of the corresponding strut 200, preferably for the entire length of the adjustment schedule. The controller modules 300 may operate fully or nearly fully autonomously, adjusting the lengths of the struts 200 over time as prescribed by the correction schedule without further user input. However, in other embodiments, a person (such as the patient or medical personnel) may serve as a gatekeeper, and interact with a program (e.g. a computer or mobile application) to control the controller modules 300. For example, a patient may log into the mobile app when it is time to perform a length adjustment, and select a particular strut, confirm the intended length adjustment, and select an option to initiate the adjustment, with the instructions being transmitted to the corresponding controller module 300 to perform the prescribed length adjustment of the particular strut 200.

From the above, it should be understood that the particular construction of struts 200 and controller modules 300 allows for the struts 200 to be fully functional for manual-only use, or for automated adjustment via controller modules 300, without needing separate styles of struts for manual versus automated adjustment modalities. Further, the manual strut operation provides for discrete rotational increments to maximize ease of use for the patient when the struts are being operated manually, with the discrete rotational functionality being fully and automatically disengaged upon coupling the controller module 300 toe the strut 200, allowing for strut length adjustment in infinitesimally small increments during automated length adjustment.

Figure 6A:
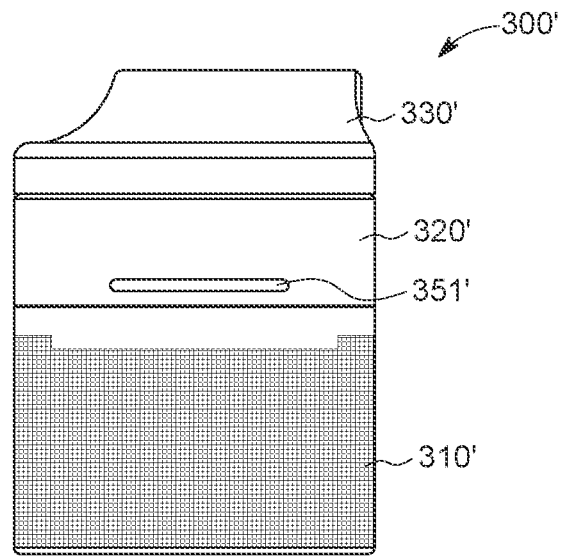
FIGS. 6A-B are front and side views of a controller module according to another embodiment of the disclosure.
Figure 6B:
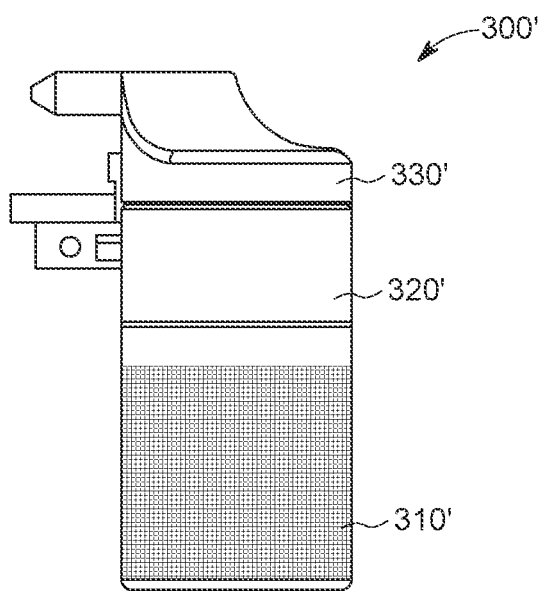

It should be understood that the struts 200 and/or controller modules 300 may take other forms while still havening similar overall functionality as described above. For example, FIGS. 6A-6B illustrate another embodiment of a controller module 300', which may be generally similar to controller module 300. Components of controller module 300' that are similar or identical to corresponding components of controller module 300 are provided with the same part number as provided for controller module 300, but with a prime designation. It should be understood that controller module 300' may be used with a strut similar or identical to strut 200, including strut 200' (described in greater detail below).

Figure 6C:
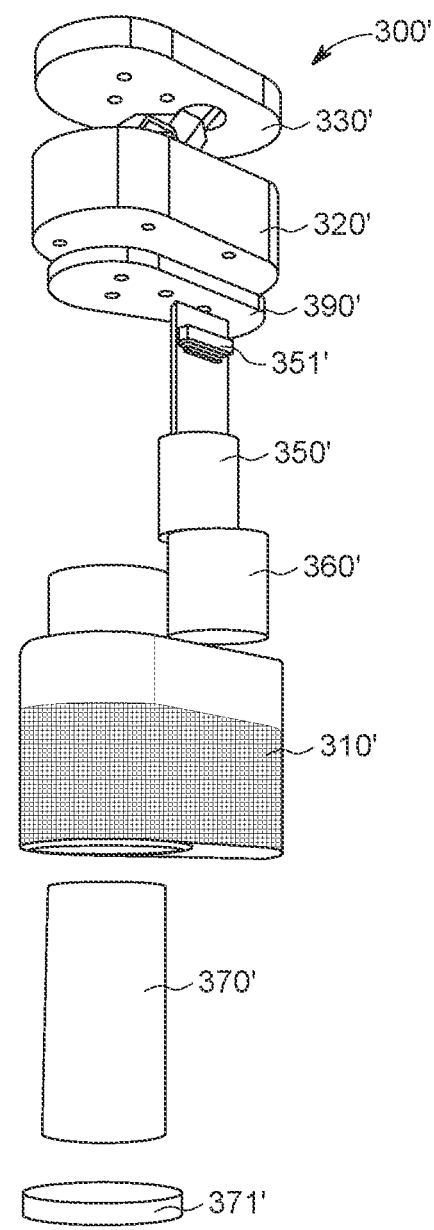
FIGS. 6C-D are exploded views of the controller module of FIGS. 6A-B.
Figure 6D:
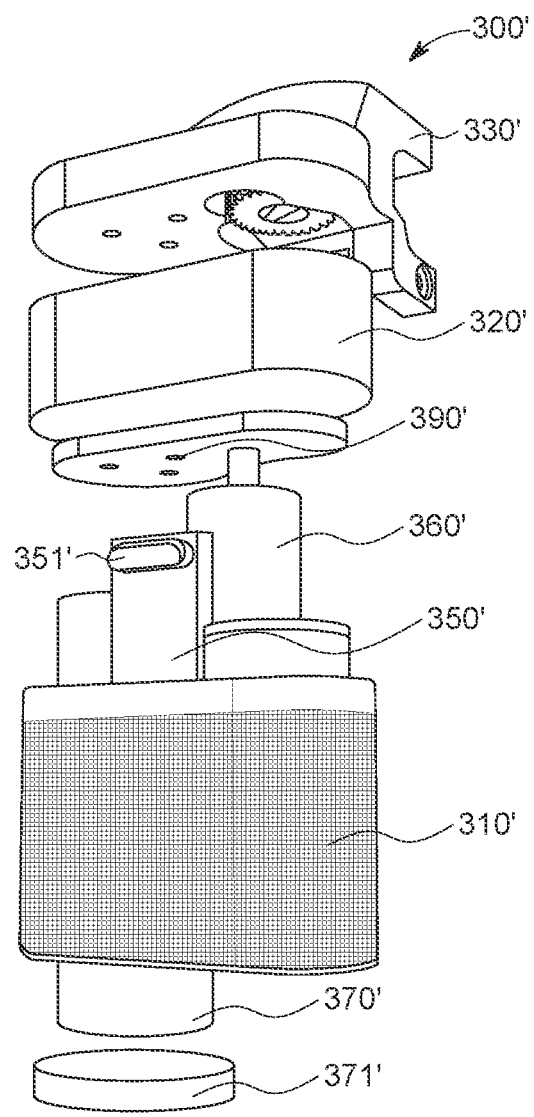

Referring to FIGS. 6A-B, as well as the exploded views of FIGS. 6C-D, controller module 300' may include a bottom housing 310', a top housing 320', and a collar 330'. A battery 370' may be housed partially or completely within lower housing 310', and may be covered by a battery cap 371' to help secure the battery 370' within the bottom housing 310'. As with controller module 300, controller module 300' may be powered by battery 370', including use of any electronics and motors therein. The controller module 300' may include one or more controllers 350' within the bottom housing 310' and/or top housing 320'. For example, a controller 350' may have a first portion positioned within bottom housing 310' and a top portion positioned within top housing 320', with a light such as an LED 351' on the controller 350' and positioned within the top housing 320' when assembled. The LED 351' may be configured to display a particular color that is visible through top housing 320' (or otherwise through a viewing area between top housing 320' and bottom housing 310', such as shown in FIG. 6H), with the color of the LED 351' being used to provide a status indicator of the controller module 300'. For example, a green light may indicate that all is well, a blue light may indicate that a blue tooth pairing mode is active, a red light may indicate a low battery, an amber light may indicate that a strut length adjustment is being actively performed, etc. It should be understood that the particular colors and the status indicated by the colors are just exemplary, and any desired color may be used to indicate any desired status of the controller module 300'. In some embodiments, the LED 351' is visible around up to all, or substantially all, of the perimeter of the controller module 300' to help ensure the LED 351' is easily viewed in any position that the controller module 300' may have relative to other components of the fixation frame. The controller module 300' may also include a motor 360' adapted to drive a gear system 340' (best shown in FIGS. 6C-D). Gear system 340' may have any suitable configuration so that actuation of the motor 360' rotates a gear of gear system 340' that meshes with gear 220 (or 220') of strut 200 (or 200'). Controller module 300' may include a mounting plate 390' that may be used to help mount components of the controller module 300' in desired relative positions and/or to one another. Mounting plate 390' may also help to seal off the inside of the controller module 300' from the external environment, which may help protect the internal components from degradation due to dust, contaminants, water ingress, etc. The protection from water ingress may be particularly helpful to allow a patient to shower while an external fixation frame utilizing the controller modules 300' is mounted to a patient's body.

Figure 6E:
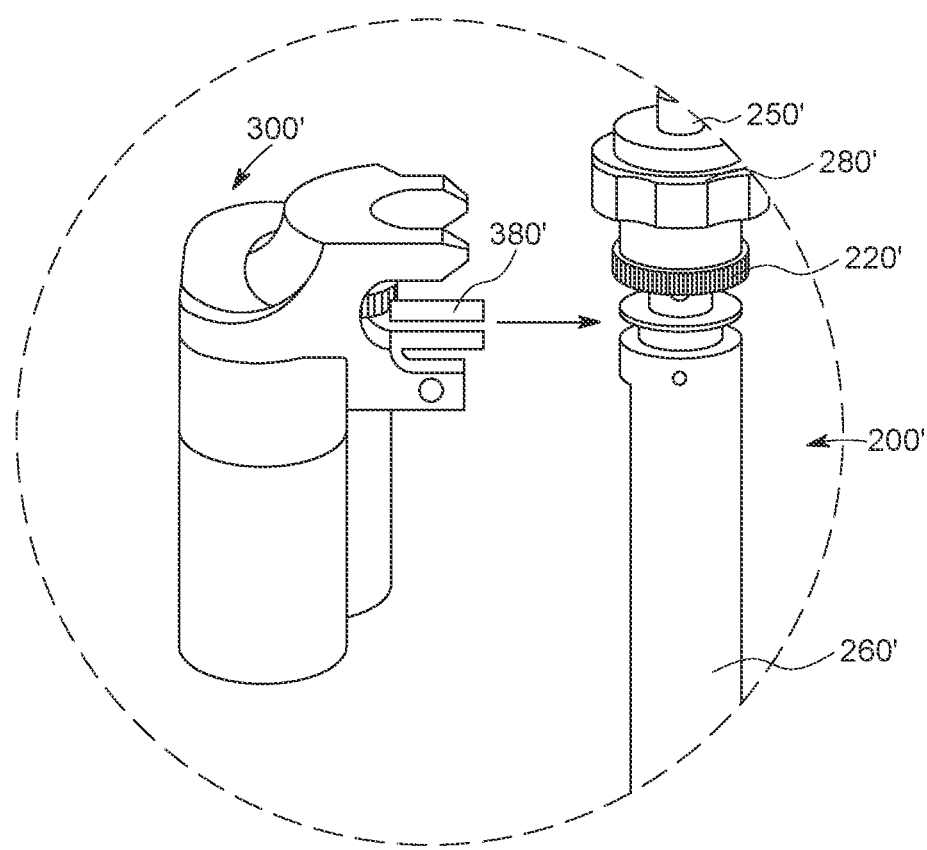
FIGS. 6E-G are views that illustrate different stages in the attachment of the controller module of FIGS. 6A-B to a strut.

FIG. 6E illustrates controller module 300' being moved toward engagement with strut 200'. Briefly, strut 200' may be generally similar to strut 200, with some slight modifications. The remaining components of strut 200' that are not described below may be similar to or identical to the corresponding components of strut 200. Strut 200' may include a generally cylindrical tube 260' into which a threaded rod 250' may translate to increase or decrease the effective length of the strut 200'. A strut gear 220' may be configured to mesh with controller module 300' in a similar or identical way that strut gear 220 interacts with controller module 300. One of the differences between strut 200' and strut 200 is the relative positioning between thumbwheel 280' and strut gear 220'. In strut 200, the thumbwheel 200 is pressed "downward" toward the strut gear 220 to compress the wave spring 290 and to disengage the contact between the flats of the "clicking mechanism" that promotes the easy incremental manual strut length adjustment described above. In strut 200', on the other hand, the thumbwheel 280' is pressed "upward" away from strut gear 220' to compress the biasing mechanism (which may be a wave spring or other spring, and which is not visible in FIG. 6E) in order to disengage the corresponding flats of the "clicking mechanism." The "clicking mechanism" of strut 200' may be substantially similar to that described in connection with strut 200, other than the particular orientation of structures like the corresponding flats being reversed. However, in some embodiments, the thumbwheel 280' and the strut gear 220' are formed as a single piece, so that rotation of either component results in rotation of the other component. Another difference is that strut 200' includes a securement area 291' having a generally square or rectangular profile adjacent an end of the tube 260' on the end near the strut gear 220', with a generally circular or cylindrical flange 292' positioned adjacent the securement area 291'. The securement area 291', with or without the cylindrical flange 292', may help better secure the controller module 300' to the strut 200', as described in more detail below. The square or rectangular profile of the securement area 291' may allow for a user to mount the controller module 300' in up to four different orientations, which may help the user mount the controller module 300' in a position that avoids interference with other components of the fixation system (such as rings or pins) or with the patient's anatomy. In other words, this profile provides the user (e.g. surgical personnel) additional flexibility in positioning the controller module 300' relative to other nearby structures. And although a square or rectangular profile is shown, other shapes, including any regular polygon, may be suitable as well. For example, a hexagonal profile may allow for up to six mounting orientations, an octagonal profile may allow for up to eight mounting orientations, etc. In some embodiments, the securement area 291' may even be circular to allow for many mounting position options. This flexibility in mounting position of the controller module 300' may not only help avoiding interference with nearby structures, buy may also help with providing clear visualization of the patient's anatomy, for example during imaging such as X-ray imaging.

Figure 6F:
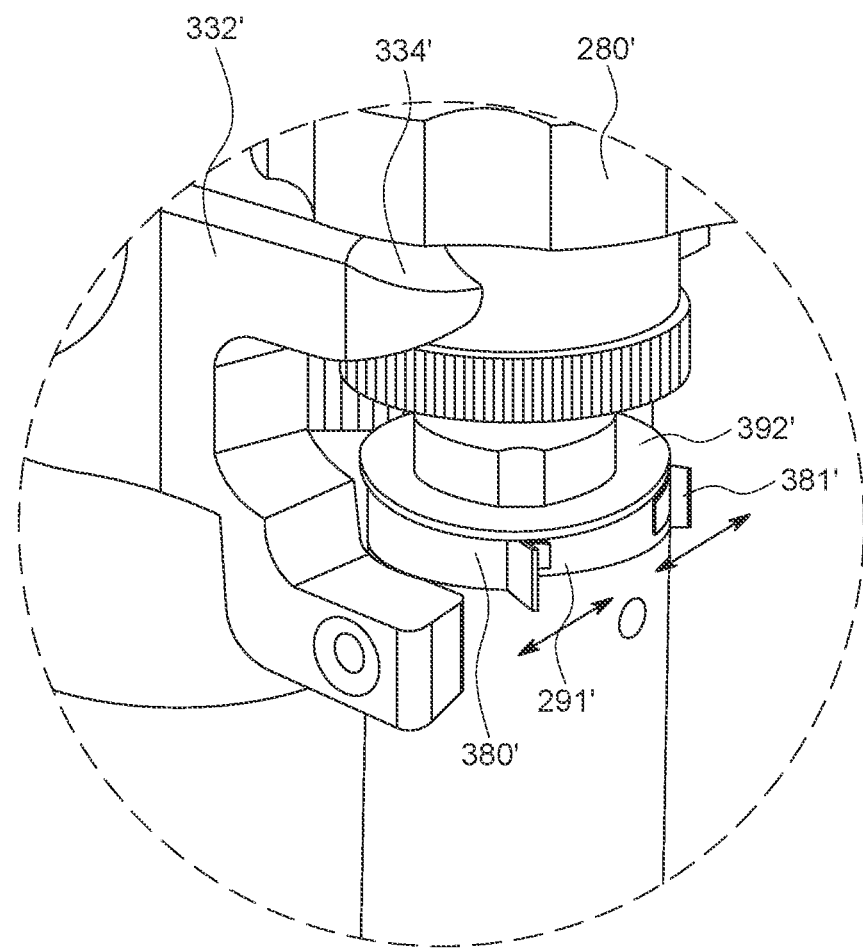

FIG. 6F illustrates the controller module 300' having been coupled to the strut 200'. Referring to both FIGS. 6E-F, controller module 300' may include a pair of cantilevered extensions 380' that are spaced apart from one another a distance that is about equal to, or slightly smaller than, the width of the securement area 291'. As best shown in FIG. 6F, the terminal end of each extension 380' may include a transverse projection 381' positioned such that the two projections 381' extend toward each other. With this configuration, the two extensions 380' may be aligned with opposite edges of the securement area 291', and as the controller module 300' is pushed toward the strut 200', the extensions 380' flex outwardly until the projections 381' clear the end of the securement area 291'. Once the projections 381' clear the end, they may "snap" back and hook around the back side of the securement area 291', providing for a "quick snap" connection between the controller module 300' and the strut 200'. If included, the flange 292' may provide an upper boundary to help ensure that the extensions 380' cannot translate up or down the strut 200'. However, in other embodiments, the extensions may have little or no flexibility.

Still referring to FIG. 6F, the collar 330' of controller module 300' may include two prongs 332' with ramped surfaces 334' that function mostly identically to the corresponding components of controller module 300. For example, as the collar 330' is advanced toward strut 200', the ramped surfaces 334' are positioned between thumbwheel 280' and strut gear 220' in order to help push the thumbwheel 280' upwards away from strut gear 220' to compress the spring and disengage the clicking mechanism. As described in connection with strut 200, this allows for a transition between manual adjustment of the strut 200' using thumbwheel 280', to automatic adjustment (in infinitesimally small increments) of the length of strut 200' via interaction between controller module 300' and strut gear 220'. The main difference, as noted above, is that the clicking mechanism is disengaged by pressing the thumbwheel 280' upward relative to the strut gear 220' instead of downward.

Figure 6G:
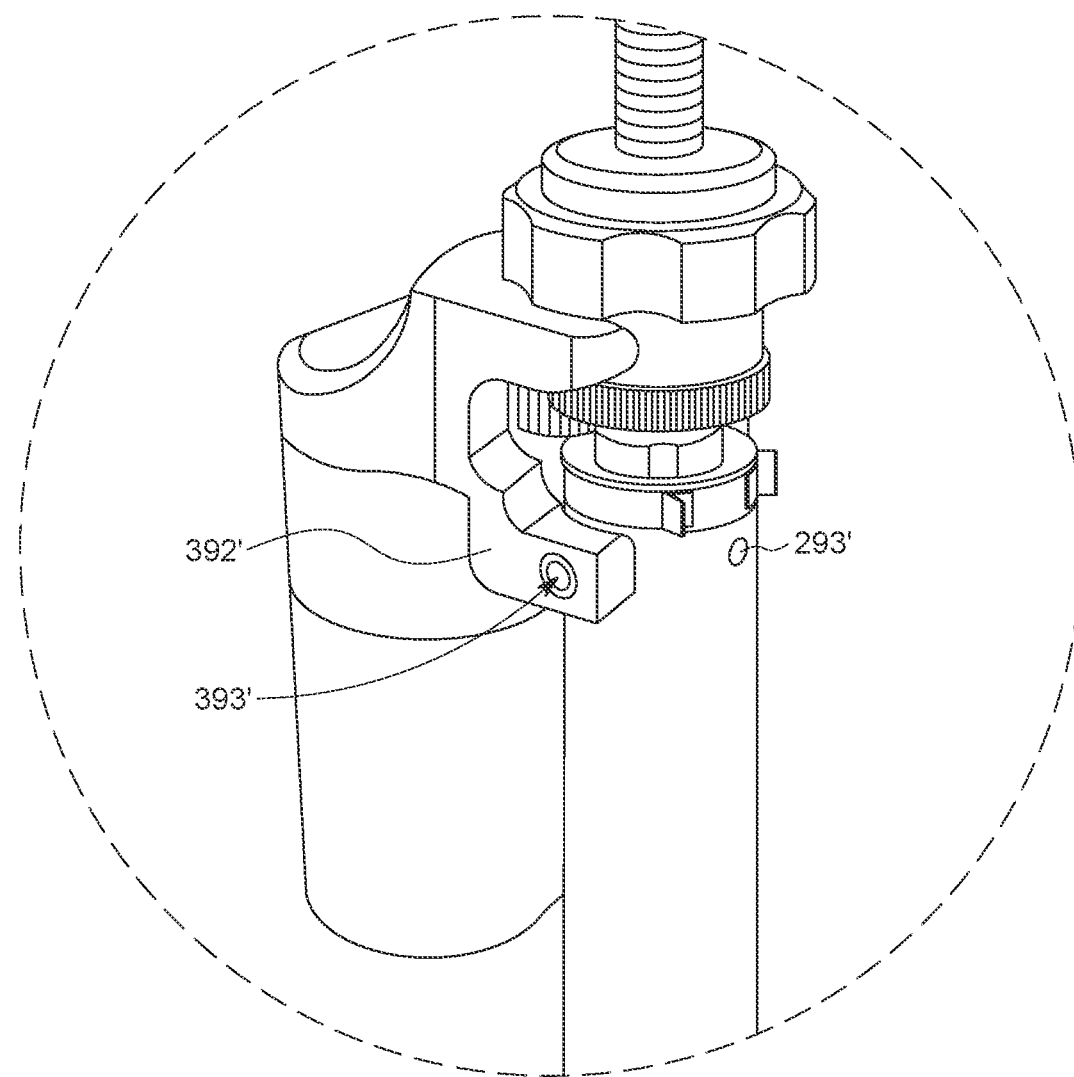
Figure 6H:
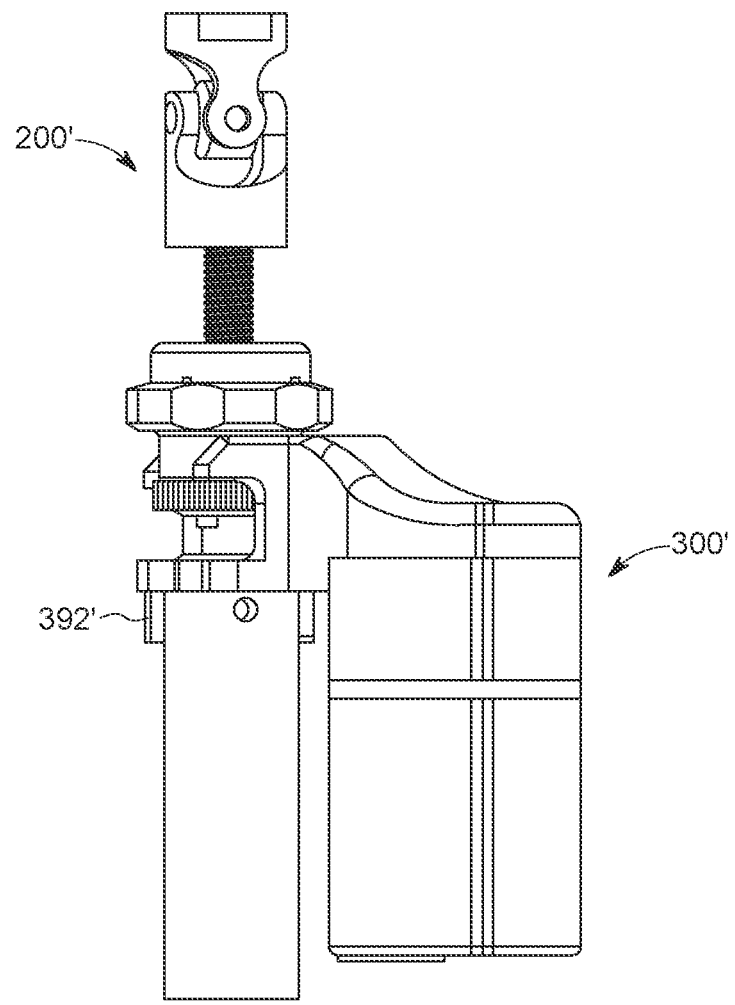
FIG. 6H is a side view of the controller module of FIGS. 6A-B coupled to the strut of FIGS. 6E-G.

Another difference between controller module 300' and controller module 300 is that additional securement of the controller module may be provided in a slightly different manner. For example, controller module 300 is shown with a fastener 336 as part of collar 330. Although controller module 300' could include a feature like this, the particular illustrated embodiment has a different particular mechanism for additional securement. For example, after the controller module 300' is connected to the strut 200' via the "quick snap" mechanism described above and as shown in FIG. 6G, the controller module 300' may be additionally secured with one or more fasteners. Controller module 300' is illustrated as having a second collar that has one (or two) prongs 392', and one or both prongs 392' may include an aperture 393' that is configured to align with one or more corresponding apertures 293' in tube 260'. The connection may be using a threaded fastener or any other suitable fastener. In some embodiments, a threaded fastener (not illustrated) may be pre-assembled to, or captured within, the aperture(s) 393' of prong(s) 392' in order to help with ease of assembly. If a threaded fastener is used, apertures 293' may include corresponding threading.

FIG. 6H is a side view of controller module 300' coupled to strut 200'. Although controller module 300' may include two prong 392', it may be preferable to include only a single prong 392', as is illustrated in FIGS. 6A-H. Because the prong 392' is mainly used for allowing the additional securement, two prongs 392' may not be necessary. In the view of FIG. 6H, the single prong 392' is positioned on the opposite side of the strut 200' that is in the foreground.

It should be understood that the method of use of controller module 300', whether used with strut 200 or strut 200', or another strut with similar features, may be substantially identical to that described above in connection with controller module 300. The only differences between the uses of controller module 300', compared to controller module 300', are the relative positions of the controller module to the strut, and the different attachment mechanisms (including the "quick snap" feature of controller module 300'). However, it should be understood the controller module 300' (and controller module 300) may be modified without departing from the inventive concepts. For example, a "quick snap" mechanism may be added to controller module 300, or removed from controller module 300'. Similarly, the securement provided by fasteners to further fix the controller module to the struts may be modified without detracting from the overall use of the controller modules.

Figure 6I:
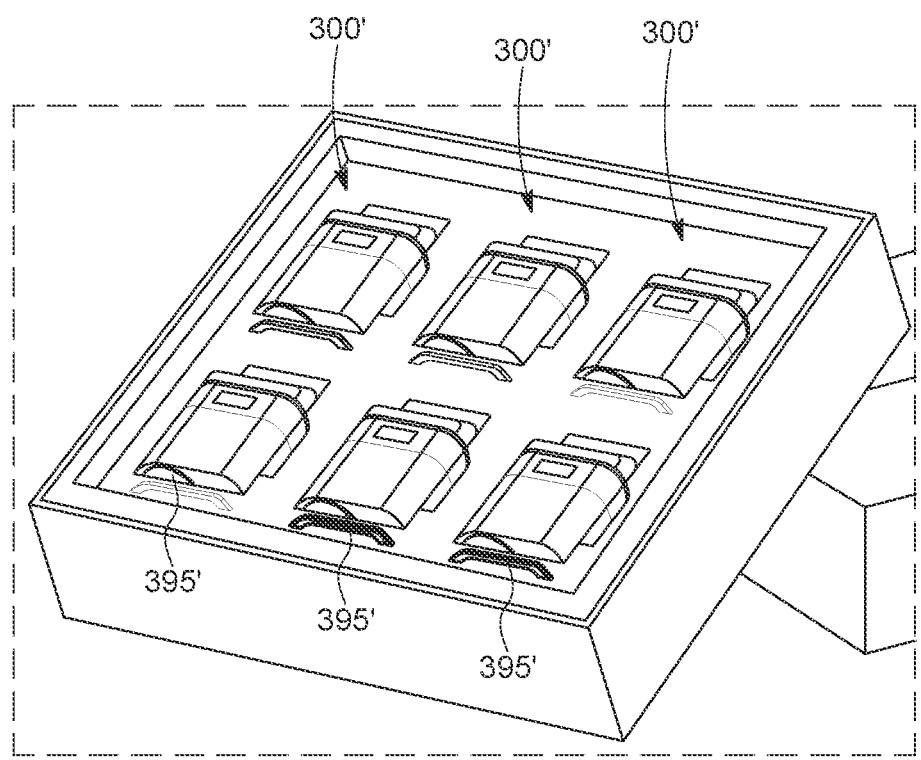
FIG. 6I is a perspective view of an exemplary kit of controller modules that include identification clips.
Figure 6J:
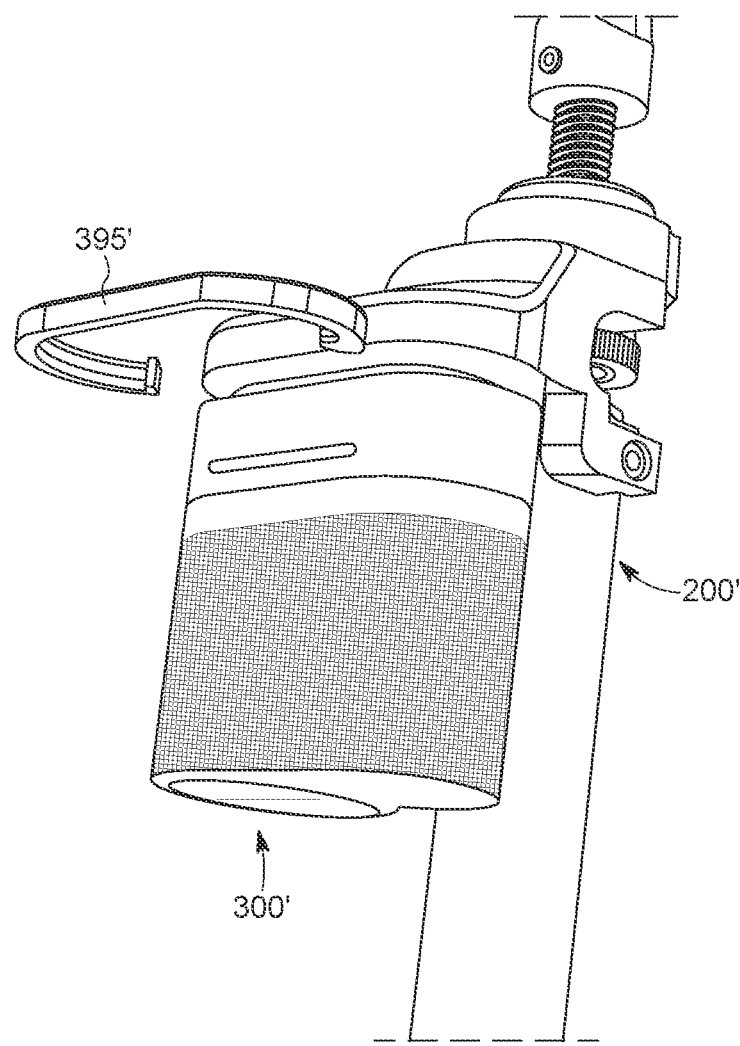
FIG. 6J is an enlarged view of an identification clip of FIG. 6I being snapped onto a corresponding controller module.

When provided to a user, such as a surgeon or patient, the controller modules 300' may be provided in a set corresponding to the number of struts 200 (or 200') used for the external fixation system 10. FIG. 6I illustrates on exemplary kit in which six identical controller modules 300' are provided in a package, corresponding to six struts 200'. In the embodiment shown in FIG. 6I, each controller module 300' can be provided with a corresponding identification clip 395'. Each identification clip 395' may be a different color, for example colors of the rainbow (red, orange, yellow, green, blue, violet). The colors of identification clips 395' may correspond to colors of strut identifiers 240, or other similar components. As shown in the enlarged view of FIG. 6J, before, after, or during attachment of controller module 300' to strut 200', an identification clip 395' may be snapped onto controller module 300'. In the illustrated example, if strut 200' includes a blue strut identifier 240, a blue identification clip 395' may be snapped onto controller module 300'. A recess may be provided between collar 330' and top housing 320' that has a complementary shape to identification clip 395' to allow for a quick snap coupling between the components. However, it should be understood that the identification clips 395', if used, may take other shapes and be coupled to corresponding controller modules 300' in other ways than that illustrated in FIG. 6J.

Figure 6K:
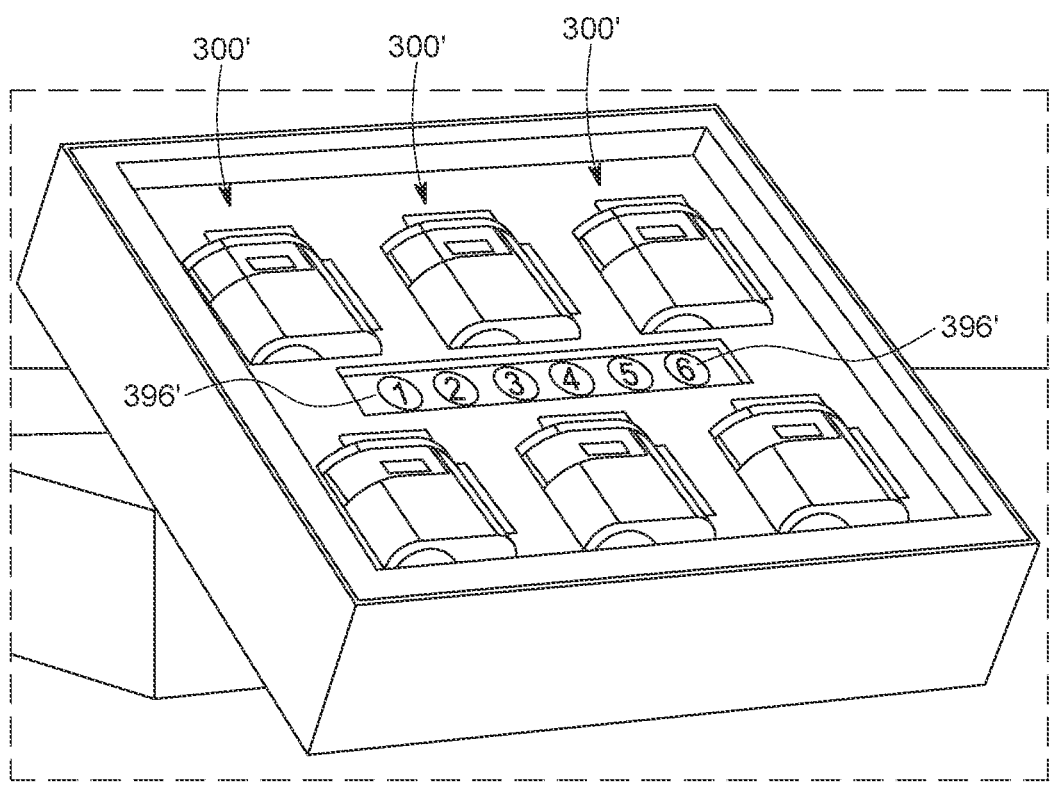
FIG. 6K a perspective view of an exemplary kit of controller modules that include identification markers.
Figure 6L:
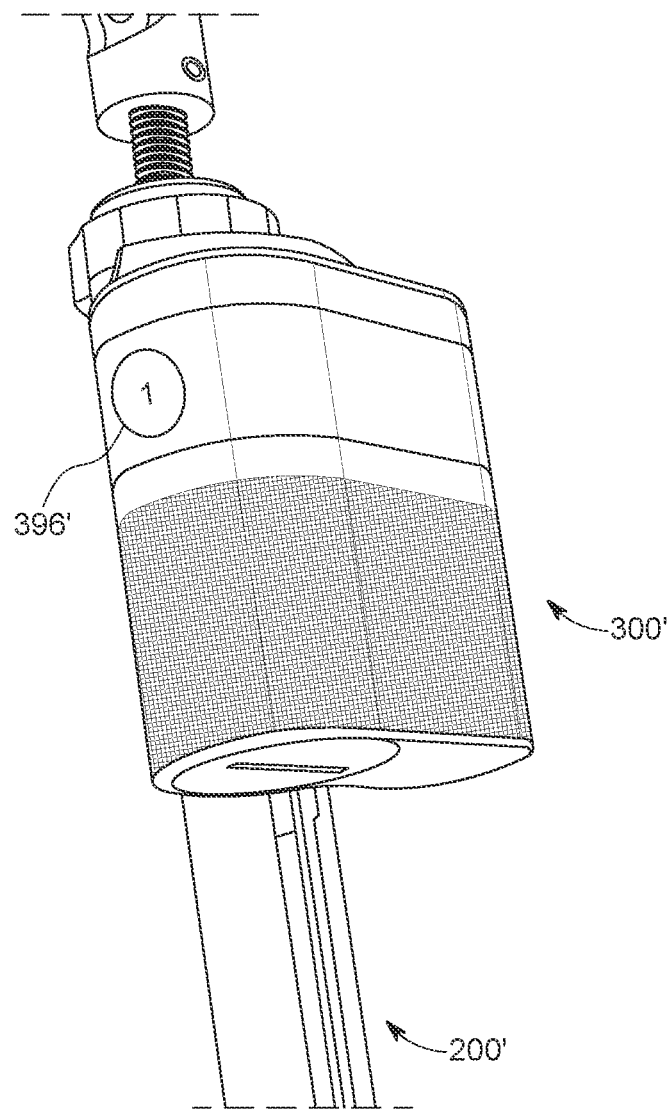
FIG. 6L is an enlarged view of an identification marker of FIG. 6K having been applied onto a corresponding controller module.

Rather than (or in addition to) the use of identification clips 395', other identification markers 396' may be provided with a set of controller modules 300'. For example, FIG. 6K illustrates a set of six controller modules 300' provided with a set of six identification markers 396'. In the particular illustrated embodiment, the identification markers 396' are stickers that include a number (e.g. one through six) and a color (e.g. colors of the rainbow). As shown in the enlarged view of FIG. 6L, before, after, or during attachment of controller module 300' to strut 200', an identification marker 396' may be applied to controller module 300'. In the illustrated example, if strut 200' includes a red (and/or number) strut identifier 240, a red identification marker 396' (which may bear a corresponding number on the strut identifier 240) may be applied to controller module 300'. Although identification markers 396' are illustrated as stickers, other types of identifiers may be provided that can be similarly applied to the controller modules 300'.

It should be understood that, if the controller modules described herein are used for a particular patient, a number of the controller modules (typically equal to the number of struts, for example six) would be used. Thus, it would be desirable to have a simple and fast way to couple the controller modules to the struts in a way that helps to ensure proper alignment, including proper engagement of the corresponding gears, while also having the ability to reduce the likelihood the controller modules will unintentionally disconnect from their corresponding struts. FIGS. 7A-E are various views of controller module 300" for attachment to strut 200'. Controller module 300" may be similar or identical to controller modules 300, 300', with the main difference being the particular way in which collar 330" is constructed. As with other embodiments herein, collar 330" may include two prongs 332" with ramped surfaces 334" that function similarly or identically to the corresponding components of controller modules 300, 300'. For example, as the collar 330" is advanced toward strut 200' (to the left in the view of FIG. 7A), the ramped surfaces 334" are positioned between thumbwheel 280' and strut gear 220' in order to help push the thumbwheel 280' upwards away from strut gear 220' to compress the spring and disengage the clicking mechanism. It should be understood that the thumbwheel 280' may also be manually pulled upward to compress the spring prior to or during advancement of the collar 330" toward strut 200'. As described above, this allows for a transition between manual adjustment of the strut 200' using thumbwheel 280', to automatic adjustment (in infinitesimally small increments) of the length of strut 200' via interaction between controller module 300" and strut gear 220'. While the prongs 332" help secure the controller module 300" to the strut 200', the main purpose of the prongs 332" is to maintain the thumbwheel 280' in the spaced position relative to the strut gear 220'. The collar 330" may include additional connector features to help with the fast and accurate securement of the controller module 300" to the strut 200', not dissimilar to those described in connection with collar 330'.

Figure 7A:
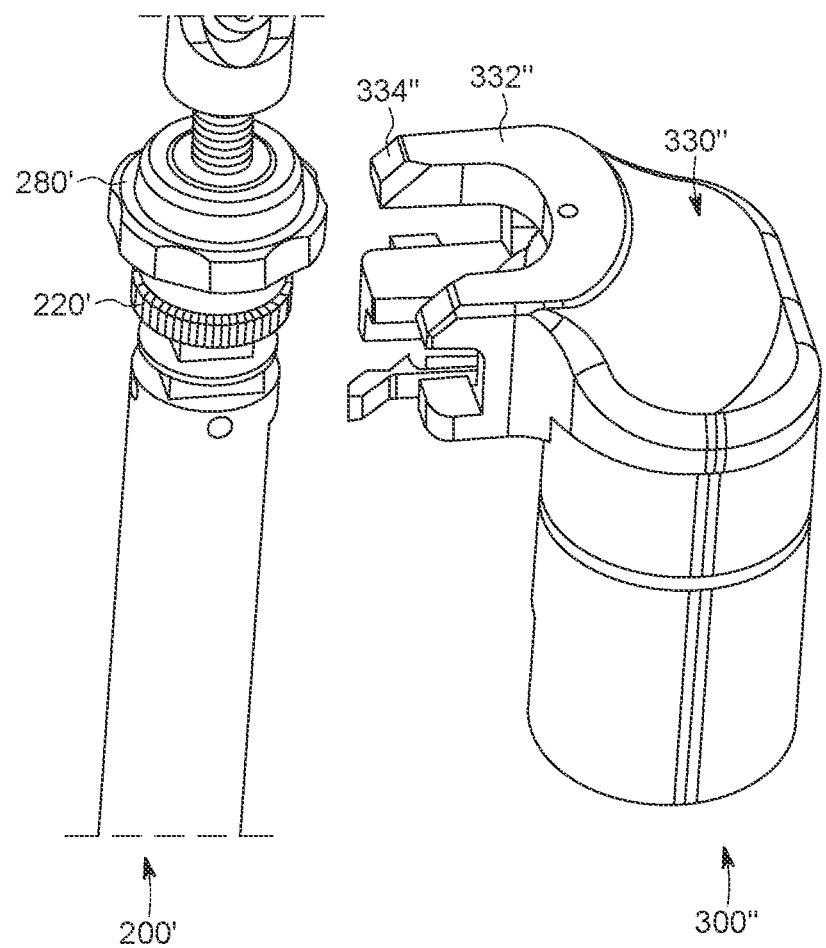
FIGS. 7A-E are views that illustrate different stages in the attachment of a controller module according to another embodiment of the disclosure to the strut of the strut of FIGS. 6E-G.
Figure 7B:
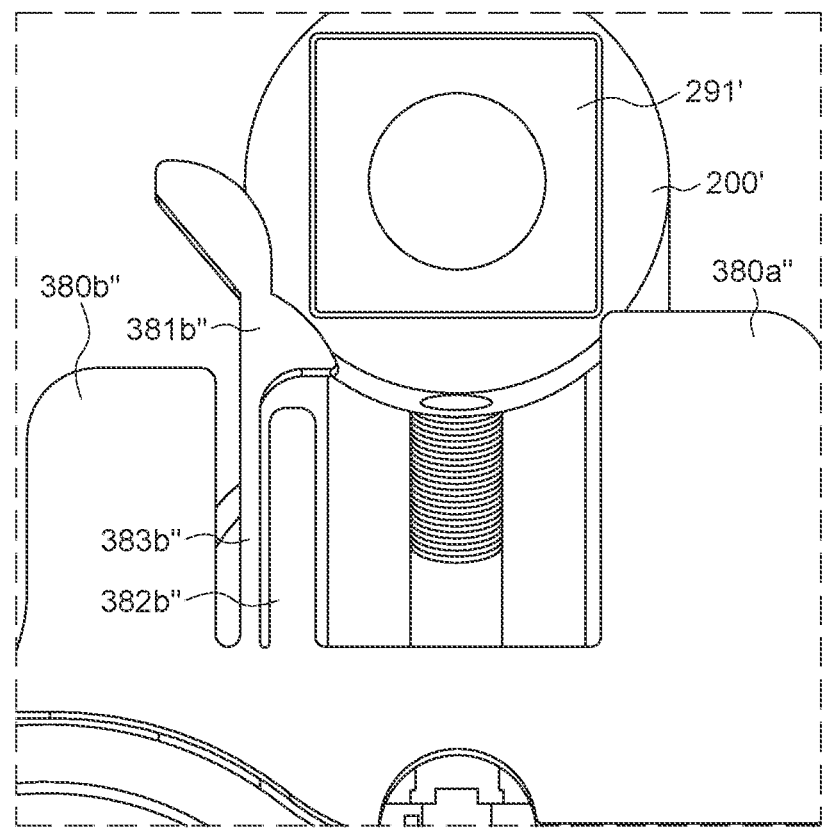
Figure 7C:
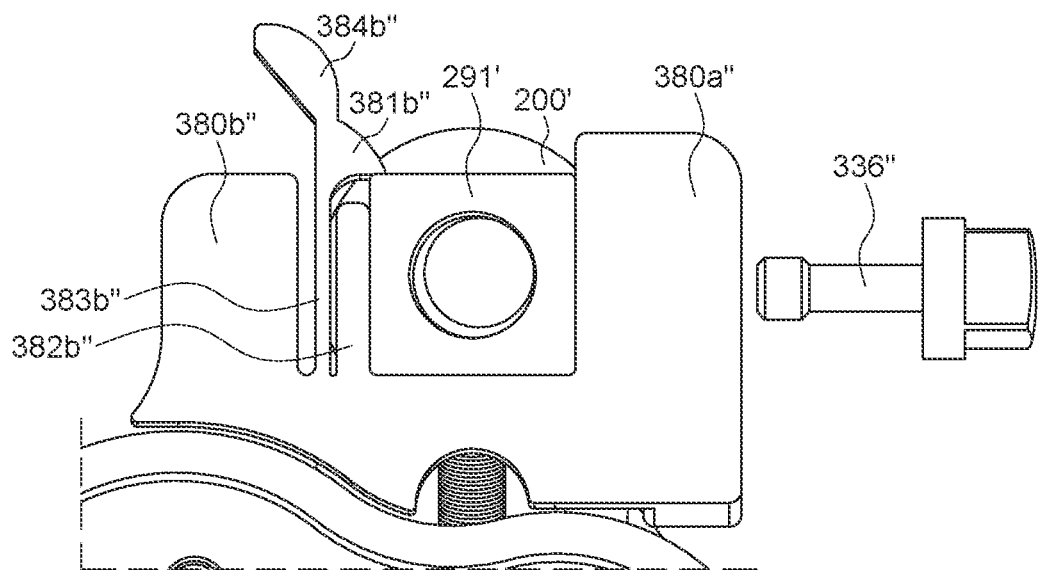

FIG. 7B illustrates a cross-section of controller module 300" just before it is attached to strut 200', the cross section passing through the generally square or rectangular securement area 291' of the strut 200'. The bottom of collar 330", generally opposite the prongs 332", may include two extensions 380a" and 380b" extending in the same direction as prongs 332". Extension 380a" may be relatively wider than extension 380b" and may be configured to abut a side edge of securement area 291' when the controller module 300" is coupled to the strut 200'. Two more extension 382b" and 383b" may be positioned adjacent extension 380b". Extension 382b" may extend in the same direction as extension 380a" and be configured to abut a side edge of securement area 291' opposite extension 380a" when the controller module 300" is coupled to the strut 200'. Extension 382b" may be thicker than the relatively thin and flexible extension 383b" (described below), creating a consistent, solid fit between securement area 291' and extensions 380a", 382b". Extension 383b" may be positioned between extensions 382b" and 380b", and extend in generally the same direction. Extension 383b" may be relatively thin and capable of deflection, and may include a transverse projection 381b" at a position that extends beyond the terminal end of extension 382b". The transverse projection 381b" may extend toward extension 380a" so that the distance between transverse projection 381b" and extension 380a" is smaller than the width of securement area 291'. With this configuration, as the collar 330" is advanced into engagement with securement area 291', contact between the securement area 291' and the transverse projection 381b" causes the extension 383b" to flex away from the securement area 291' to provide clearance to continue advancing the controller module 300". Once the controller module 300" is fully advanced, and the transverse projection 381b" clears the end of securement area 291' (as shown in FIG. 7C), the extension 383b" can "un-flex" or snap back to its unbiased condition, with the transverse projection 381b" hooking around the back end of the securement area 291'. This may result in an audible "click" confirming the connection, and may provide at least minimal impediment to the controller module 300" from being pulled away from the strut 200' unintentionally. The extension 383b" may include a grip 384b" that may allow the user to force the extension 383b" to flex away from the securement area 291' if the user wants to disconnect the controller module 300" from the strut 200'. The extension 380b" may be positioned to limit the amount that the extension 383b" may flex away from the securement area 291', which may help ensure that the extension 383b" does not over-flex and break or snap off from the collar 330".

Although the transverse projection 381b" may provide some resistance to disconnection between the controller module 300" and the strut 200', it is desirable (but not fully necessary) to have even more protection from unintentional disconnection between the controller module 300" and the strut 200'. To that end, a fastener 336" may be provided with collar 330", as either a separate device or as a captured component that cannot fully disconnect from the collar 330". Similar to controller module 300', after the controller module 300" is connected to the strut 200' via the "quick snap" mechanism described above and as shown in FIG. 7C, the controller module 300" may be additionally secured fastener 336". Extension 380a" may include an aperture that is configured to align with a corresponding aperture 293' in tube 260'. The fastener 336" may be a threaded fastener, but other types of fastening mechanisms may be suitable. If a threaded fastener is used, apertures 293' may include corresponding threading.

Figure 7D:
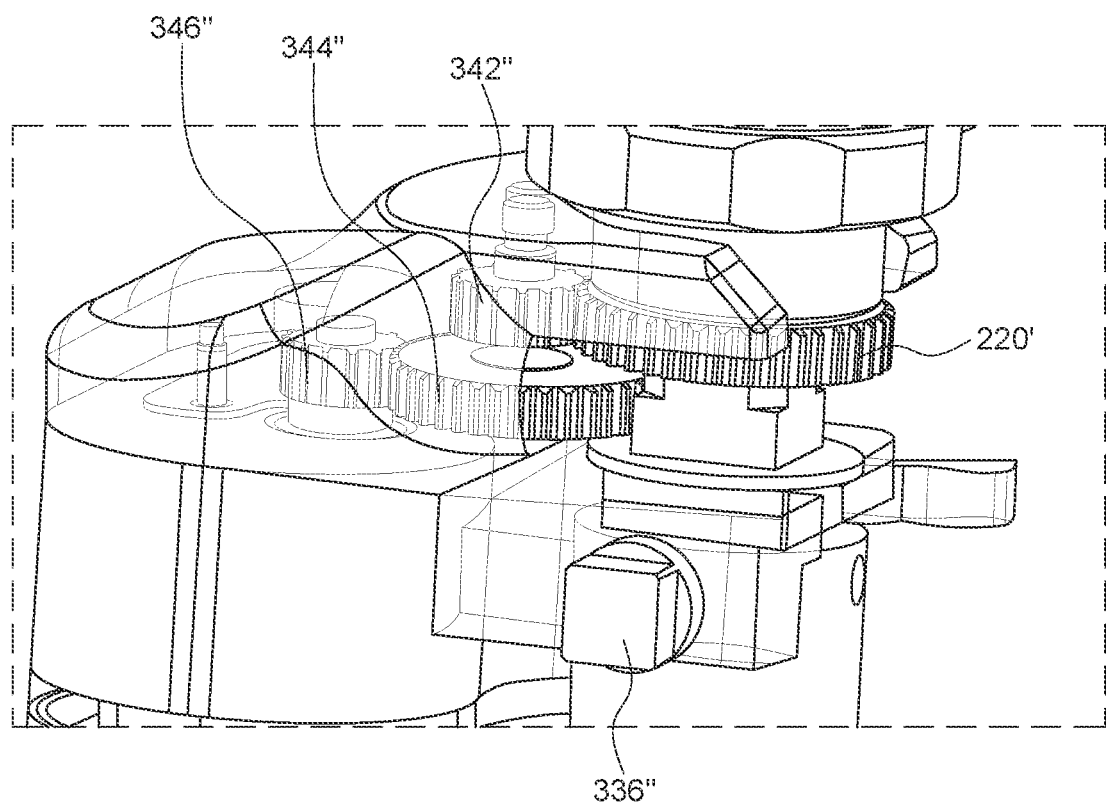
Figure 7E:
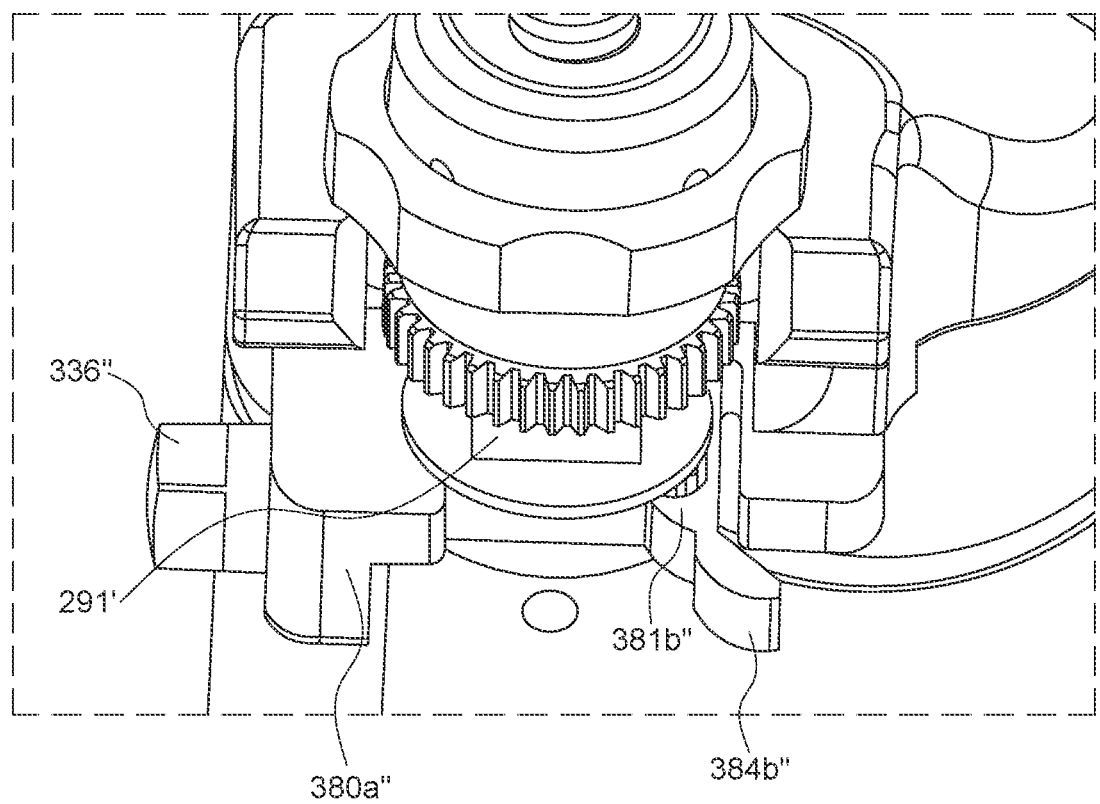

FIGS. 7D-E illustrate controller module 300" after being coupled to strut 200', including via use of fastener 336". FIG. 7E illustrates particularly well the way in which the various components of collar 330" interact with strut 200', while FIG. 7D (which shows collar 330" as transparent) illustrates the connection between strut gear 220' and small gear 342", as well as relative positions of the large gear 344" and the motor gear 346".

As should be understood from the above, the collar 330" allows for quick attachment of the controller module 300" to the strut 200' in a way which helps guarantee the proper positioning and interaction of the controller gears with the strut gear, with the fastener 336" allowing for longer term securement between the controller module 300" and the strut 200' after the initial connection. The configuration described above may minimize the time and difficulty involved in coupling each controller module 300" to each corresponding strut 200', while helping to ensure that connection occurs in the correct manner, and allowing for additional securement via fastener 336" to help avoid unintentional disconnection.

Although one particular clip-style collar 330" is described above, it should be understood that other configurations and mechanisms may be used to allow for a simple and fast way to couple the controller modules to the struts, including in ways that help ensure proper alignment between the controller modules and the struts. For example, simple threaded connections between the controller module and the struts, or magnetic couplings between the controller module and the struts, may help to provide fast and secure attachment of the controller modules to the struts.

As should be understood from the above, one of the main benefits of the controller modules 300, 300', 300" described above is that it allows for switching between manual and automatic modes of operation of struts, in which the manual mode of operation allows for manual lengthening or shortening of the strut via discrete incremental length adjustments, and the automatic mode of operation allows for automatic, motor-controlled lengthening or shortening of the strut via infinitesimally small incremental length adjustments. However, the ability to adjust strut lengths in infinitesimally small increments provides for techniques that are not possible with other modes of strut operation, explained in more detail below.

Dynamization refers to small, quick, movements (or vibrations) of the length of a strut during a correction process. Axial dynamization of struts may stimulate the bone callus at the osteotomy site, improving bone quality and healing time during and after correction. Current adjustable length struts on the market typically may be adjusted in length by a minimum of about 0.25 mm using incremental adjustment. In other words, the minimum amount that a commercially available strut may be lengthened (or shortened) at a time is about 0.25 mm. Some fixation systems include separate components to provide for dynamization, but such systems typically require additional components that are specifically designed to allow for dynamization. For example, some systems include a mechanism that essentially "loosens" the struts in an axial direction, which may allow for slight axial movement of the strut when the patient walks and loads the frame. However, this dynamization is not consistent, controlled, or specific. Further, it may be burdensome to add these dynamization-specific features, and these features may even cause pain to the patient. Still further, the current dynamization-specific features that may be used or only configured for use after the bone adjustment is complete, and the bone is in the "consolidation" phase at the end of correction. This is because the current dynamization products typically work by destabilizing the frame, and the frame should not be destabilized during the correction phase. And simply manually adjusting the length of the strut in any particular sequence will not be effective for dynamization, because effective dynamization requires length changes that are smaller and more frequent than possible with known struts that allow for manual length adjustment.

When the controller modules described above are coupled to any of the struts described above, the strut becomes "unlocked" from the manual incremental length adjustment and infinitesimally small length adjustment becomes possible. This feature may be leveraged to create a dynamization feature or program using any of the controller modules described above. For example, during the actual correction process, and not just at the end of the correction process, the controller modules may move some or all of the struts up and down (e.g. lengthen and shorten) at very small increments (e.g. less than 0.25 mm) and at a rapid pace to achieve dynamization of the struts.

An exemplary use of any of the controller modules described above is provided below, with the use of dynamization described, although it should be understood that dynamization could also be omitted. A patient that requires bone correction via an external fixation frame may undergo surgery to attach the external fixation system to the patient, for example two fixation rings coupled to portions of the bone and six telescopic struts coupling the two fixation rings together. It should be understood that more or fewer struts may be used, and more than two fixation rings may be used, and the term fixation "ring" does not necessarily imply a closed circular ring, but may apply to open rings as well. After the surgery is complete, preferably outside the sterile operating theater, medical personnel may quickly snap a controller module onto each strut of the fixation system as described above, with the gear(s) of each controller module engaging or intermeshing with the strut gear upon connection. Further, upon connection, the manual adjustment "clicking mechanism" is disengaged and the strut switches to an automatic adjustment mode that allows for length adjustment in infinitesimally small increments. Prior to, during, or after coupling the controller modules to the corresponding struts, the medical personnel should confirm that each controller module is coupled to the "correct" strut. In other words, each controller module will be responsible for adjusting (and possibly dynamizing) a particular strut—so it is important that any correction schedule uploaded to (or otherwise associated with) a particular controller module reflects the correction schedule for the particular strut to which that controller module is coupled. Stickers, colored snap-on rings, or other indicia may be applied to the strut(s) and/or the controller module(s) to help ensure that each controller module is coupled to the corresponding strut which it is intended to control. The correction schedule may be uploaded to (or otherwise associated with) each controller module either prior to, during, or after the coupling of the controller modules to the struts.

Prior to, during, or after confirming that each controller module is coupled to the correct corresponding strut, further securement may be provided, for example by using a fastener to further fix each controller module to each corresponding strut. However, in some circumstances, the additional fastener may be omitted.

Once the controller modules are secured to the correct struts, and the desired correction plans are uploaded to (or otherwise associated with) the controller modules, the patient may be ready for the correction to begin. In some scenarios, the patient (or a caregiver of the patient) may be provided with software, such as an application on a computer (including a mobile device such as a smart phone), that assists with control of the correction. For example, each time that a length adjustment is required, the application may send an alert to the user, and the software may assist the user in initiating the different length adjustments, for example by guiding the user to select a particular strut, and confirm on the application that the strut adjustment should be performed according to the correction schedule. Upon confirmation, the software may communicate (e.g. wirelessly or via wires) with the controller module, with the controller module motor causing the controller module gears to rotate the desired amount, and thus the strut gear to rotate the desired amount to cause the strut length to change the desired amount. Once complete, the software may mark that particular adjustment as completed, and may even communicate with the patient's physician to confirm that the strut adjustment is complete. The process may be repeated for each strut until the particular correction is completed, and the process may be repeated for each correction in the entire schedule until the correction is finalized.

It should be understood that, in other embodiments, each individual strut length adjustment according to the correction plan may instead be pushed from a physician, instead of being under the patient's control. Even further, the correction plan may instead be fully automated, so that the individual length adjustments do not need to be individually activated by the patient (or a caregiver or physician).

During the performance of the correction plan, including before the struts have reached their final desired lengths, dynamization may be performed. Similar to strut length adjustment, dynamization may be initiated via interaction with software (by the patient, a caregiver, or a physician). For example, at any desired time schedule, the software may alert the user that dynamization should be performed, and the user may interact with the software to confirm that dynamization should proceed. Upon confirmation, the controller modules may increase and decreases the lengths of the struts in small increments with a desired pace for a desired total duration to stimulate the bone callus. In other uses, the dynamization may be automatically performed without any additional input by the user (or a caregiver or physician). As should be understood, the strut length changes during dynamization are typically smaller than the minimum length change increment typically available in manual strut length adjustment systems, which is typically 0.25 mm. At the end of each individual dynamization period, the strut length may end at the same length the strut was at the beginning of the dynamization period. After the correction plan is complete (e.g. after the struts have reached their final desired lengths), and the bone is in the "consolidation phase," dynamization may be performed at any desired schedule. As should be understood from the description above, the ability to perform strut dynamization during the correction phase has not been successfully performed previously, and the controller modules and their uses described herein allow for such dynamization to occur during the correction phase without losing frame stability. The accuracy and precision of dynamization permitted by the systems described herein, regardless of when the dynamization is being performed relative to the correction schedule, has also not been known previously.

Figure 8A:
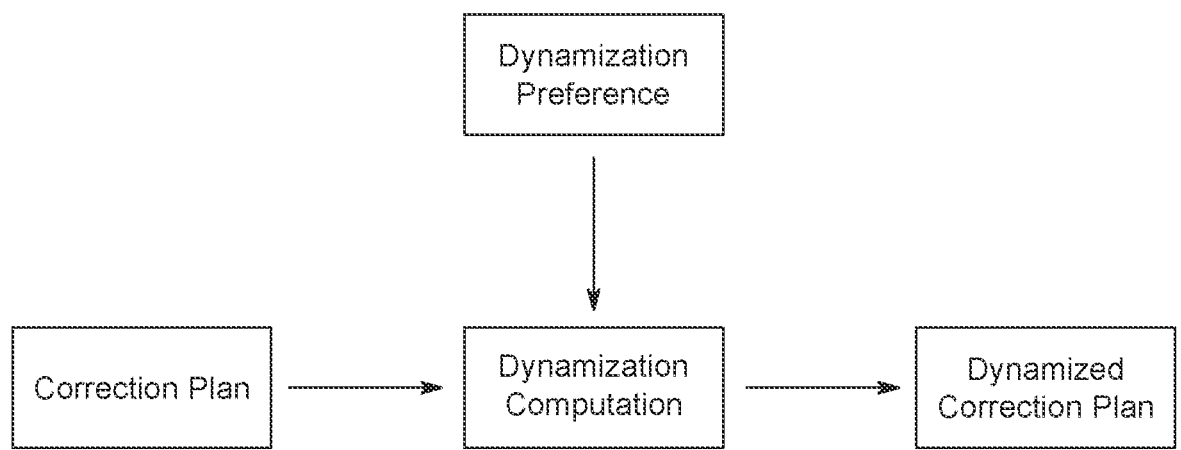
FIGS. 8A-B are flowcharts illustrate use cases of a dynamization program during a correction plan.
Figure 8B:
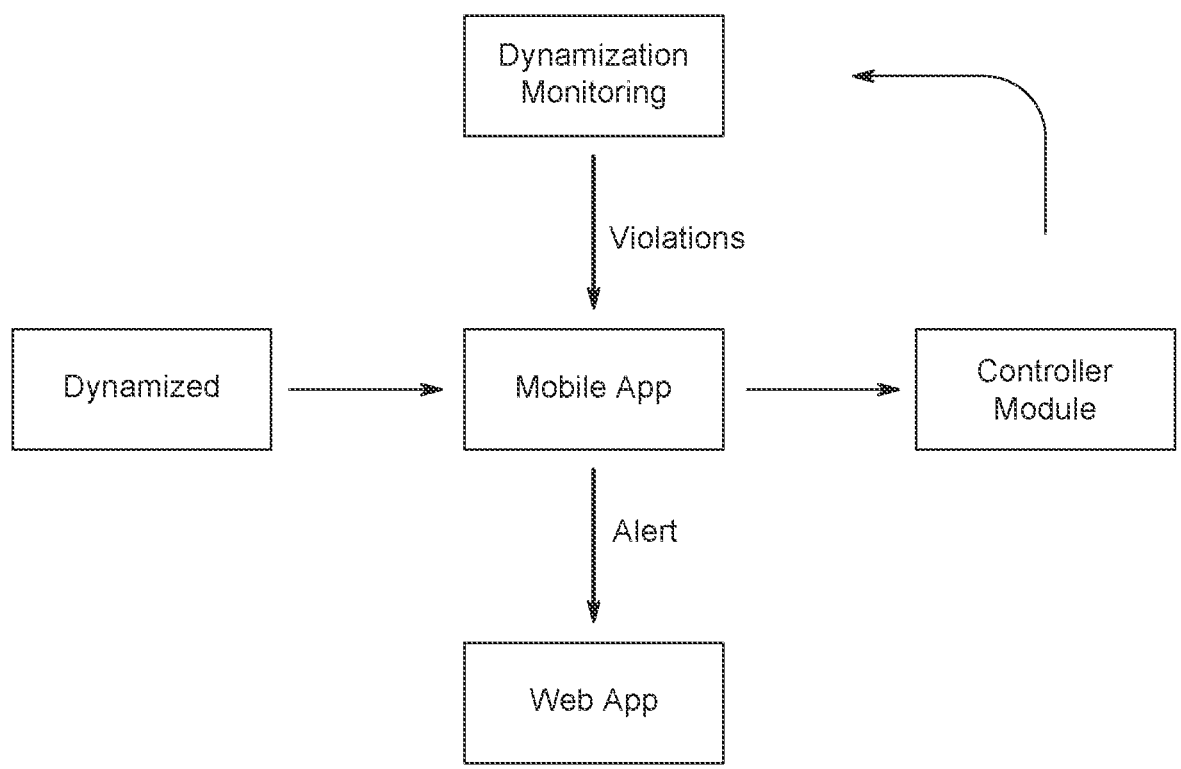

FIGS. 8A-B illustrate two flow charts related to the use of dynamization as part of the bone correction. For example, FIG. 8A illustrates that the physician (or other medical personnel) may set a particular dynamization preference (e.g. frequency with which dynamization is performed, parameters for each individual dynamization such as amplitude, pace, and total duration of the individual dynamization) may be set. The "amplitude" of dynamization may refer to the length change of the strut during the dynamization. For example, during a particular dynamization effort, the strut length may increase length and then decrease length by 0.1 or 0.01 mm, which would be the amplitude. These values are merely exemplary, and any desired amplitude may be used. The "pace" may refer to the time it takes for one cycle of the dynamization to be complete. For example, the speed with which the strut increases and then decreases length (for a single cycle), may be referred to as the pace, and any desired pace may be set for the dynamization. The total duration of each individual dynamization effort may refer to how long a dynamization effort lasts. For example, if 100 cycles are performed in each dynamization effort over a period of 30 minutes, the duration of the dynamization is 30 minutes. The frequency of the dynamization may refer to how often a dynamization effort is performed. For example, this may be once between each scheduled length adjustment, twice between each scheduled length adjustment, etc. Alternatively, the frequency may be input on a time basis, e.g. every 4 hours, every 6 hours, every 12 hours, etc. As shown in FIG. 8A, these dynamization preferences may be input into software by a user, and the dynamization preferences may be combined with the correction plan to compute how the dynamization is incorporated into the correction plan, in order to output a final dynamized correction plan.

Dynamization may also be monitored via the controller modules. For example, as shown in the flowchart of FIG. 8B, dynamization may be initiated, for example, by the patient (or a caregiver) using a mobile application, which may instruct the controller module to perform the dynamization. The controller module (and/or the mobile application) may also monitor the actual process of dynamization, and if any conditions of dynamization are violated, the mobile app may be informed of such violation, which in turn may be output to an application under the control or supervision of a physician, for example a web application available to the physician. Violations to be reported may include various examples. For example, if the controller module "jams," or otherwise malfunctions, an alert may be output. In another example, deviations from the prescription dynamization protocol by surgeon, an alert may be output. In this example, as described above, controlled, cyclical interfragmentary micromotion during the initial stages of the bone healing may beneficially produce callus and early bridging. Excessive motion during the latter stages of healing, however, may have a detrimental effect on the union as it prolongs the chondral phase of healing. This excessive motion, if detected, may cause an alert to be created. Such a system may provide the patient the ability to control and monitor the dynamization, but importantly may alert the patient's physician to any abnormalities that the physician may need to address. In another example of dynamization, the controller modules may actuate struts at different lengths. If the external fixation frame is a neutral frame, all struts could be actuated simultaneously by the same amount for dynamization. However, in an angulated or rotated frame, different lengths of each strut may be needed to achieve a prescribed axial micromotion in the osteotomy site. The controller modules and systems described herein would allow for such different strut length changes to achieve a desired prescribed axial micromotion at the osteotomy site in an angulated or rotated frame construct.

As should be understood from the description above, the struts and controller modules described herein allow for either manual strut length adjustment, or for automated strut length adjustment, without the need for any additional hardware components beyond the controller modules. Thus, the controller modules may be omitted from a particular correction altogether. In some situations, although it may not be optimal, the option may remain to switch from a manual adjustment mode to an automated adjustment mode (or vice versa) by coupling the controller modules to the struts (or removing the controller modules from the struts), after the correction schedule has begun.

Although the invention herein has been described with reference to particular embodiments, it is to be understood that these embodiments are merely illustrative of the principles and applications of the present invention. For example, features described in relation to one particular embodiment may be combined with features of other embodiments described herein. It is therefore to be understood that numerous modifications may be made to the illustrative embodiments and that other arrangements may be devised without departing from the spirit and scope of the present invention as defined by the appended claims.

The invention claimed is:

1. An external fixation system comprising:
a first fixation ring configured to couple to a first bone portion of a patient;
a second fixation ring configured to couple to a second bone portion of the patient;
a plurality of adjustable length struts, each adjustable length strut having a first joint proximate a first end of the strut, a second joint proximate a second end of the strut opposite the first end, a rod, a tube that receives the rod, and an actuator configured to drive the rod axially relative to the tube to change an effective length of the strut; and
a plurality of controller modules, each controller module configured to couple to a corresponding strut;
wherein in an assembled condition of the external fixation system, the plurality of struts couple the first fixation ring to the second fixation ring;
the external fixation system has a manual mode of operation in which there is no coupling between any of the plurality of controller modules and any of the plurality of struts, and manual actuation of one of the actuators is configured to change the effective length of the corresponding strut in discrete length increments; and
the external fixation system has an automated mode of operation in which each of the controller modules is coupled to the corresponding strut, and automated actuation of one of the actuators is configured to change the effective length of the corresponding strut in infinitesimally small length increments,
wherein the actuator of each strut includes a strut knob and a strut gear, the strut knob being translatable relative to the strut gear between a first axial position relative to the strut gear and a second axial position relative to the strut gear,
wherein when the strut knob is in the first axial position relative to the strut gear, the strut knob is constrained from rotation relative to the strut, and when the strut knob is in the second axial position relative to the strut gear, the strut knob is rotatable relative to the strut.

2. The external fixation system of claim 1, wherein in the manual mode of operation, a biasing member biases the strut knob to the first axial position.

3. The external fixation system of claim 2, wherein in the manual mode of operation, each discrete length increment corresponds to a discrete increment of rotation of the strut knob relative to the strut.

4. The external fixation system of claim 3, wherein in the manual mode of operation, when the strut knob is in the second axial position relative to the strut gear, the biasing member is prevented from transitioning the strut knob to the first axial position between each discrete increment of rotation.

5. The external fixation system of claim 1, wherein in the automated mode of operation, the controller module maintains the strut knob in the second axial position relative to the strut gear.

6. The external fixation system of claim 5, wherein in the automated mode of operation, a controller gear of the controller module interfaces with the strut gear.

7. The external fixation system of claim 6, wherein each controller module includes a motor configured to rotate the controller gear.

8. The external fixation system of claim 7, wherein each controller module includes a collar with at least one prong, and when the controller module is coupled to the corresponding strut, the at least one prong is positioned between the strut gear and the strut knob.

9. The external fixation system of claim 8, wherein the at least one prong includes a tip portion with a ramped surface, the ramped surface configured to drive the strut knob to the second axial position as the controller module is coupled to the corresponding strut.

10. The external fixation system of claim 8, wherein the collar includes a first extension and a second extension defining a distance therebetween, the distance being about equal to a width of a securement area of the strut, the first and second extensions configured to abut the securement area of the strut when the controller module is coupled to the strut to secure the controller module to the strut.

11. The external fixation system of claim 10, wherein the first extension is flexible and includes a transverse projection extending toward the second extension, a reduced distance between the transverse projection and the second extension being smaller than the width of the securement area of the strut.

12. The external fixation system of claim 11, wherein, as the controller module is coupled to the strut, contact between the transverse projection and the securement area of the strut is configured to cause the first extension to flex away from the strut until the transverse projection clears an end of the securement area and the first extension snaps back toward the securement area so that the transverse projection impedes the controller module from uncoupling from the strut.

13. The external fixation system of claim 7, wherein when the external fixation system is in the automated mode of operation, each controller module has a dynamization mode configured to cycle between increasing and decreasing the effective length of the strut to axially dynamize the strut with effective length adjustments that are smaller than the discrete length increments in the manual mode of operation.

14. The external fixation system of claim 13, wherein in the assembled condition of the external fixation system, the external fixation system has a stable construction, and while each controller module is operating in the dynamization mode cycling between increasing and decreasing the effective length of the corresponding strut, the external fixation system remains in the stable construction.

15. A method of implementing a correction plan to correct a deformity in a bone of a patient, the method comprising:
coupling a first fixation ring to a first portion of the bone of the patient;
coupling a second fixation ring to a second bone portion of the bone of the patient;
coupling the first fixation ring to the second fixation ring with a plurality of adjustable length struts, each strut having a first joint proximate a first end of the strut, a second joint proximate a second end of the strut opposite the first end, a rod, a tube that receives the rod, and an actuator configured to drive the rod axially relative to the tube to change an effective length of the strut; and providing a plurality of controller modules, each controller module configured to couple to a corresponding strut;

wherein the correction plan may be implemented using either (i) a manual mode of operation or (ii) an automated mode of operation;

wherein in the manual mode of operation, there is no coupling between any of the plurality of controller modules and any of the plurality of struts, and manual actuation of one of the actuators changes the effective length of the corresponding strut in discrete length increments; and wherein in the automated mode of operation, each of the controller modules is coupled to the corresponding strut, and automated actuation of one of the actuators is capable of changing the effective length of the corresponding strut in infinitesimally small length increments, coupling the plurality of controller modules to the corresponding struts, and implementing the correction plan using the automated mode of operation, and operating one of the controller modules in a dynamization mode to cycle between increasing and decreasing the effective length of the corresponding strut to axially dynamize the strut with effective length adjustments that are smaller than the discrete length increments available in the manual mode of operation.

16. The method of claim 15, wherein operating one of the controller modules in the dynamization mode is performed during a correction phase in which all of the plurality of struts have not yet reached a corresponding final effective length.

17. The method of claim 16, wherein operating one of the controller modules in the dynamization mode is also performed in a consolidation phase in which all of the plurality of struts have reached the corresponding final effective length.

* * * * *